(12) United States Patent
Alvarez et al.

(10) Patent No.: US 10,980,669 B2
(45) Date of Patent: Apr. 20, 2021

(54) METHOD, APPARATUS AND SYSTEM FOR A WATER JET

(71) Applicant: Auris Health, Inc., Redwood City, CA (US)

(72) Inventors: Jeffery B. Alvarez, Redwood City, CA (US); David Mintz, Mountain View, CA (US)

(73) Assignee: Auris Health, Inc., Redwood City, CA (US)

( * ) Notice: Subject to any disclaimer, the term of this patent is extended or adjusted under 35 U.S.C. 154(b) by 0 days.

(21) Appl. No.: 16/257,980

(22) Filed: Jan. 25, 2019

(65) Prior Publication Data

US 2019/0151148 A1 May 23, 2019

Related U.S. Application Data

(63) Continuation of application No. 14/158,548, filed on Jan. 17, 2014, now Pat. No. 10,231,867.

(Continued)

(51) Int. Cl.
*A61F 9/007* (2006.01)
*A61B 17/3203* (2006.01)
*A61B 34/30* (2016.01)

(52) U.S. Cl.
CPC ...... *A61F 9/00736* (2013.01); *A61B 17/3203* (2013.01); *A61B 34/30* (2016.02)

(58) Field of Classification Search
CPC .. A61F 9/007; A61F 9/00736; A61B 17/3203; A61B 17/32037; A61B 2017/32002; A61B 2017/32032; A61B 2017/32035; A61B 34/30; A61B 34/32; A61B 34/35; A61B 34/37; A61B 34/70; A61B 34/71; A61B 34/73; A61B 34/74; A61B 34/75; A61B 34/76; A61B 34/77;
(Continued)

(56) References Cited

U.S. PATENT DOCUMENTS

| 3,763,860 A | 10/1973 | Clarke |
| 4,040,413 A | 8/1977 | Ohshiro |

(Continued)

FOREIGN PATENT DOCUMENTS

| CN | 101443069 | 5/2009 |
| CN | 100515347 | 7/2009 |

(Continued)

OTHER PUBLICATIONS

Balicki, et al. Single fiber optical coherence tomography microsurgical instruments for computer and robot-assisted retinal surgery. Medical Image Computing and Computer-Assisted Intervention. MICCAI 2009. Springer Berlin Heidelberg, 2009. 108-115.

(Continued)

*Primary Examiner* — Katrina M Stransky
*Assistant Examiner* — Kankindi Rwego
(74) *Attorney, Agent, or Firm* — Chang & Hale LLP

(57) ABSTRACT

A water jet instrument may be used for manually performing surgery. The water jet instrument may be manually controlled or controlled by a system with a robotic control. The water jet apparatus defines a jet cutting area that is based at least in part on a flow rate meter and a feedback loop.

14 Claims, 19 Drawing Sheets

Related U.S. Application Data

(60) Provisional application No. 61/754,426, filed on Jan. 18, 2013.

(58) Field of Classification Search
CPC ........ A61B 2034/301; A61B 2034/302; A61B 2034/303; A61B 2034/304; A61B 2034/305; A61B 2034/306; A61B 2034/715; A61B 2034/731; A61B 2034/732; A61B 2034/733; A61B 2034/741; A61B 2034/742; A61B 2034/744
USPC ........................................ 137/15.14; 606/107
See application file for complete search history.

(56) References Cited

U.S. PATENT DOCUMENTS

| | | |
|---|---|---|
| 4,198,960 A | 4/1980 | Utsugi |
| 4,470,407 A | 9/1984 | Hussein |
| 4,532,935 A | 8/1985 | Wang et al. |
| 4,597,388 A | 7/1986 | Koziol et al. |
| 4,685,458 A | 8/1987 | Leckrone |
| 4,747,405 A | 5/1988 | Leckrone |
| 4,854,301 A | 8/1989 | Nakajima |
| 4,898,574 A | 2/1990 | Uchiyama et al. |
| 4,905,673 A | 3/1990 | Pimiskern |
| 4,983,165 A | 1/1991 | Loiterman |
| 5,029,574 A | 7/1991 | Shimamura et al. |
| 5,085,659 A | 2/1992 | Rydell |
| 5,196,023 A | 3/1993 | Martin |
| 5,217,465 A | 6/1993 | Steppe |
| 5,308,323 A | 5/1994 | Sogawa et al. |
| 5,318,589 A | 6/1994 | Lichtman |
| 5,325,848 A | 7/1994 | Adams et al. |
| 5,342,381 A | 8/1994 | Tidemand |
| 5,344,395 A | 9/1994 | Whalen et al. |
| 5,353,783 A | 10/1994 | Nakao et al. |
| 5,370,609 A | 12/1994 | Drasler et al. |
| 5,372,124 A | 12/1994 | Takayama et al. |
| 5,411,016 A | 5/1995 | Kume |
| 5,425,735 A | 6/1995 | Rosen et al. |
| 5,431,649 A | 7/1995 | Mulier et al. |
| 5,441,485 A | 8/1995 | Peters |
| 5,449,356 A | 9/1995 | Walbrink |
| 5,450,843 A | 9/1995 | Moll et al. |
| 5,472,406 A | 12/1995 | De La Torre et al. |
| 5,472,426 A | 12/1995 | Bonati et al. |
| 5,496,267 A * | 3/1996 | Drasler ............ A61B 17/32037 604/22 |
| 5,501,667 A | 3/1996 | Verduin, Jr. |
| 5,520,684 A | 5/1996 | Imran |
| 5,545,170 A | 8/1996 | Hart |
| 5,562,648 A | 10/1996 | Peterson |
| 5,562,678 A | 10/1996 | Booker |
| 5,572,999 A | 11/1996 | Funda et al. |
| 5,573,535 A | 11/1996 | Viklund |
| 5,613,973 A | 3/1997 | Jackson et al. |
| 5,645,083 A | 7/1997 | Essig et al. |
| 5,653,374 A | 8/1997 | Young et al. |
| 5,658,311 A | 8/1997 | Baden |
| 5,662,590 A | 9/1997 | De La Torre et al. |
| 5,695,500 A | 12/1997 | Taylor et al. |
| 5,697,949 A | 12/1997 | Giurtino et al. |
| 5,710,870 A | 1/1998 | Ohm |
| 5,716,325 A | 2/1998 | Bonutti |
| 5,788,667 A | 8/1998 | Stoller |
| 5,792,165 A | 8/1998 | Klieman |
| 5,797,900 A | 8/1998 | Madhani |
| 5,810,770 A | 9/1998 | Chin et al. |
| 5,893,869 A | 4/1999 | Barnhart |
| 5,897,491 A | 4/1999 | Kastenbauer et al. |
| 5,924,175 A | 7/1999 | Lippitt |
| 5,989,230 A | 11/1999 | Frassica |
| 6,033,371 A | 3/2000 | Torre et al. |
| 6,071,281 A | 6/2000 | Burnside et al. |
| 6,093,157 A | 7/2000 | Chandrasekaran |
| 6,110,171 A | 8/2000 | Rydell |
| 6,120,476 A | 9/2000 | Fung et al. |
| 6,120,498 A | 9/2000 | Jani et al. |
| 6,156,030 A | 12/2000 | Neev |
| 6,174,318 B1 | 1/2001 | Bates et al. |
| 6,206,903 B1 | 3/2001 | Ramans |
| 6,183,435 B1 | 6/2001 | Bumbalough et al. |
| 6,322,557 B1 | 11/2001 | Nikolaevich |
| 6,326,616 B1 | 12/2001 | Andrien et al. |
| 6,375,635 B1 * | 4/2002 | Moutafis ............ A61B 17/3203 604/22 |
| 6,394,998 B1 | 5/2002 | Wallace et al. |
| 6,398,792 B1 | 6/2002 | O'Connor |
| 6,405,078 B1 | 6/2002 | Moaddeb et al. |
| 6,406,486 B1 | 6/2002 | De La Torre et al. |
| 6,436,107 B1 | 8/2002 | Wang et al. |
| 6,440,061 B1 | 8/2002 | Wenner et al. |
| 6,508,823 B1 | 1/2003 | Gonon |
| 6,522,906 B1 | 2/2003 | Salisbury et al. |
| 6,554,793 B1 | 4/2003 | Pauker et al. |
| 6,577,891 B1 | 6/2003 | Jaross et al. |
| 6,638,246 B1 | 10/2003 | Naimark et al. |
| 6,671,581 B2 | 12/2003 | Niemeyer et al. |
| 6,676,668 B2 | 1/2004 | Mercereau et al. |
| 6,685,698 B2 | 2/2004 | Morley et al. |
| 6,706,050 B1 | 3/2004 | Giannadakis |
| 6,736,784 B1 | 5/2004 | Menne et al. |
| 6,763,259 B1 | 7/2004 | Hauger et al. |
| 7,087,061 B2 | 8/2006 | Chernenko et al. |
| 7,282,055 B2 | 10/2007 | Tsuruta |
| 7,344,528 B1 | 3/2008 | Tu et al. |
| 7,351,193 B2 | 4/2008 | Forman et al. |
| 7,559,934 B2 | 7/2009 | Teague et al. |
| 7,725,214 B2 | 5/2010 | Diolaiti |
| 7,736,356 B2 | 6/2010 | Cooper et al. |
| 7,882,841 B2 * | 2/2011 | Aljuri .................... A61B 18/04 128/898 |
| 7,883,475 B2 | 2/2011 | Dupont et al. |
| 7,963,911 B2 | 6/2011 | Turliuc |
| 7,967,799 B2 | 6/2011 | Boukhny |
| 7,987,046 B1 | 7/2011 | Peterman |
| 8,002,713 B2 | 8/2011 | Heske |
| 8,038,598 B2 | 10/2011 | Khachi |
| 8,049,873 B2 | 11/2011 | Hauger et al. |
| 8,092,397 B2 | 1/2012 | Wallace et al. |
| 8,187,173 B2 | 5/2012 | Miyoshi |
| 8,224,484 B2 | 7/2012 | Swarup et al. |
| 8,257,303 B2 | 9/2012 | Moll et al. |
| 8,414,564 B2 | 4/2013 | Goldshleger et al. |
| 8,480,595 B2 | 7/2013 | Speeg |
| 8,518,024 B2 | 8/2013 | Williams et al. |
| 8,523,762 B2 | 9/2013 | Miyamoto et al. |
| 8,540,748 B2 | 9/2013 | Murphy et al. |
| 8,820,603 B2 | 9/2014 | Shelton et al. |
| 8,827,948 B2 | 9/2014 | Romo et al. |
| 8,882,660 B2 | 11/2014 | Phee et al. |
| 8,945,163 B2 | 2/2015 | Voegele et al. |
| 8,956,280 B2 | 2/2015 | Eversull et al. |
| 9,173,713 B2 | 11/2015 | Hart et al. |
| 9,254,123 B2 | 2/2016 | Alvarez et al. |
| 9,345,456 B2 | 5/2016 | Tsonton et al. |
| 9,460,536 B2 | 10/2016 | Hasegawa et al. |
| 9,504,604 B2 | 11/2016 | Alvarez |
| 9,561,083 B2 | 2/2017 | Yu et al. |
| 9,592,042 B2 | 3/2017 | Titus |
| 9,597,152 B2 | 3/2017 | Schaeffer |
| 9,622,827 B2 | 4/2017 | Yu et al. |
| 9,636,184 B2 | 5/2017 | Lee et al. |
| 9,713,509 B2 | 7/2017 | Schuh et al. |
| 9,727,963 B2 | 8/2017 | Mintz et al. |
| 9,730,757 B2 | 8/2017 | Brudniok |
| 9,737,371 B2 | 8/2017 | Romo et al. |
| 9,737,373 B2 | 8/2017 | Schuh |
| 9,744,335 B2 | 8/2017 | Jiang |
| 9,763,741 B2 | 9/2017 | Alvarez et al. |
| 9,788,910 B2 | 10/2017 | Schuh |
| 9,844,412 B2 | 12/2017 | Bogusky et al. |

(56) References Cited

U.S. PATENT DOCUMENTS

| | | |
|---|---|---|
| 9,867,635 B2 | 1/2018 | Alvarez et al. |
| 9,918,681 B2 | 3/2018 | Wallace et al. |
| 9,931,025 B1 | 4/2018 | Graetzel et al. |
| 9,949,749 B2 | 4/2018 | Noonan et al. |
| 9,955,986 B2 | 5/2018 | Shah |
| 9,962,228 B2 | 5/2018 | Schuh et al. |
| 9,980,785 B2 | 5/2018 | Schuh |
| 9,993,313 B2 | 6/2018 | Schuh et al. |
| 10,016,900 B1 | 7/2018 | Meyer et al. |
| 10,022,192 B1 | 7/2018 | Ummalaneni |
| 10,080,576 B2 | 9/2018 | Romo et al. |
| 10,136,959 B2 | 11/2018 | Mintz et al. |
| 10,145,747 B1 | 12/2018 | Lin et al. |
| 10,149,720 B2 | 12/2018 | Romo |
| 10,159,532 B1 | 12/2018 | Ummalaneni |
| 10,159,533 B2 | 12/2018 | Moll et al. |
| 10,169,875 B2 | 1/2019 | Mintz et al. |
| 10,482,599 B2 | 11/2019 | Mintz et al. |
| 10,517,692 B2 | 12/2019 | Eyre et al. |
| 10,524,866 B2 | 1/2020 | Srinivasan |
| 10,639,114 B2 | 5/2020 | Schuh |
| 2002/0019644 A1 | 2/2002 | Hastings |
| 2002/0111608 A1 | 8/2002 | Baerveldt |
| 2002/0111621 A1 | 8/2002 | Wallace et al. |
| 2003/0004455 A1 | 1/2003 | Kadziauskas |
| 2003/0040681 A1 | 2/2003 | Ng et al. |
| 2003/0065358 A1 | 4/2003 | Frecker |
| 2003/0109877 A1 | 6/2003 | Morley |
| 2003/0109889 A1 | 6/2003 | Mercereau |
| 2003/0158545 A1 | 8/2003 | Hovda et al. |
| 2003/0208189 A1 | 11/2003 | Payman |
| 2004/0030349 A1 | 2/2004 | Boukhny |
| 2004/0143253 A1 | 7/2004 | Vanney |
| 2004/0153093 A1 | 8/2004 | Donovan |
| 2004/0158261 A1 | 8/2004 | Vu |
| 2004/0186349 A1 | 9/2004 | Ewers |
| 2004/0193146 A1 | 9/2004 | Lee et al. |
| 2004/0210116 A1 | 10/2004 | Nakao |
| 2004/0253079 A1 | 12/2004 | Sanchez |
| 2005/0033270 A1 | 2/2005 | Ramans et al. |
| 2005/0054900 A1 | 3/2005 | Mawn |
| 2005/0070844 A1 | 3/2005 | Chow et al. |
| 2005/0159645 A1 | 7/2005 | Bertolero |
| 2005/0240178 A1 | 10/2005 | Morley et al. |
| 2005/0261705 A1 | 11/2005 | Gist |
| 2006/0015133 A1 | 1/2006 | Grayzel |
| 2006/0058813 A1 | 3/2006 | Teague |
| 2006/0116693 A1 | 6/2006 | Weisenburgh |
| 2006/0135963 A1 | 6/2006 | Kick |
| 2006/0156875 A1 | 7/2006 | McRury et al. |
| 2006/0189891 A1 | 8/2006 | Waxman et al. |
| 2007/0016164 A1 | 1/2007 | Dudney et al. |
| 2007/0027443 A1 | 2/2007 | Rose |
| 2007/0027534 A1 | 2/2007 | Bergheim |
| 2007/0032906 A1 | 2/2007 | Sutherland et al. |
| 2007/0106304 A1 | 5/2007 | Hammack |
| 2007/0135763 A1 | 6/2007 | Musbach et al. |
| 2007/0135803 A1 | 6/2007 | Belson |
| 2007/0208375 A1 | 9/2007 | Nishizawa |
| 2007/0213668 A1 | 9/2007 | Spitz |
| 2007/0239178 A1 | 10/2007 | Weitzner et al. |
| 2007/0250111 A1 | 10/2007 | Lu |
| 2007/0299427 A1 | 12/2007 | Yeung et al. |
| 2008/0015566 A1 | 1/2008 | Livneh |
| 2008/0021440 A1 | 1/2008 | Solomon |
| 2008/0033467 A1 | 2/2008 | Miyamoto et al. |
| 2008/0046122 A1 | 2/2008 | Manzo et al. |
| 2008/0065109 A1 | 3/2008 | Larkin |
| 2008/0065111 A1 | 3/2008 | Blumenkranz |
| 2008/0097293 A1 | 4/2008 | Chin et al. |
| 2008/0114341 A1 | 5/2008 | Thyzel |
| 2008/0125698 A1 | 5/2008 | Greg et al. |
| 2008/0177285 A1 | 7/2008 | Brock et al. |
| 2008/0187101 A1 | 8/2008 | Gertner |
| 2008/0196533 A1 | 8/2008 | Bergamasco |
| 2008/0228104 A1 | 9/2008 | Uber et al. |
| 2009/0012507 A1 | 1/2009 | Culbertson et al. |
| 2009/0030446 A1 | 1/2009 | Measamer |
| 2009/0036900 A1 | 2/2009 | Moll |
| 2009/0043305 A1 | 2/2009 | Brodbeck |
| 2009/0062602 A1 | 3/2009 | Rosenberg et al. |
| 2009/0082634 A1 | 3/2009 | Kathrani et al. |
| 2009/0088774 A1 | 4/2009 | Swarup et al. |
| 2009/0105723 A1 | 4/2009 | Dillinger |
| 2009/0131885 A1 | 5/2009 | Akahoshi |
| 2009/0161827 A1 | 6/2009 | Gertner et al. |
| 2009/0171271 A1 | 7/2009 | Webster et al. |
| 2009/0227998 A1* | 9/2009 | Aljuri ............... A61B 17/32037 606/13 |
| 2009/0248041 A1 | 10/2009 | Williams et al. |
| 2009/0248043 A1 | 10/2009 | Tierney et al. |
| 2009/0264878 A1 | 10/2009 | Carmel et al. |
| 2009/0268015 A1 | 10/2009 | Scott et al. |
| 2009/0270760 A1 | 10/2009 | Leimbach et al. |
| 2009/0287188 A1 | 11/2009 | Golden et al. |
| 2009/0299352 A1 | 12/2009 | Zerfas |
| 2009/0312768 A1 | 12/2009 | Hawkins et al. |
| 2009/0326322 A1 | 12/2009 | Diolaiti |
| 2010/0004642 A1 | 1/2010 | Lumpkin |
| 2010/0010504 A1 | 1/2010 | Simaan et al. |
| 2010/0011900 A1 | 1/2010 | Burbank |
| 2010/0011901 A1 | 1/2010 | Burbank |
| 2010/0036294 A1 | 2/2010 | Mantell et al. |
| 2010/0073150 A1 | 3/2010 | Olson et al. |
| 2010/0082017 A1 | 4/2010 | Zickler |
| 2010/0114115 A1 | 5/2010 | Schlesinger et al. |
| 2010/0179632 A1 | 7/2010 | Bruszewski et al. |
| 2010/0204605 A1 | 8/2010 | Blakley |
| 2010/0204646 A1 | 8/2010 | Plicchi et al. |
| 2010/0217235 A1 | 8/2010 | Thorstenson |
| 2010/0225209 A1 | 9/2010 | Goldberg |
| 2010/0228191 A1 | 9/2010 | Alvarez et al. |
| 2010/0228249 A1 | 9/2010 | Mohr |
| 2010/0268211 A1 | 10/2010 | Manwaring et al. |
| 2010/0280320 A1 | 11/2010 | Alvarez et al. |
| 2010/0280525 A1 | 11/2010 | Alvarez et al. |
| 2010/0312141 A1 | 12/2010 | Keast et al. |
| 2010/0331858 A1 | 12/2010 | Simaan et al. |
| 2011/0009779 A1 | 1/2011 | Romano et al. |
| 2011/0015483 A1 | 1/2011 | Barbagli |
| 2011/0015648 A1 | 1/2011 | Alvarez et al. |
| 2011/0028887 A1 | 2/2011 | Fischer et al. |
| 2011/0040404 A1 | 2/2011 | Diolaiti et al. |
| 2011/0046441 A1 | 2/2011 | Wiltshire et al. |
| 2011/0071541 A1 | 3/2011 | Prisco et al. |
| 2011/0071543 A1 | 3/2011 | Prisco et al. |
| 2011/0106102 A1 | 5/2011 | Balicki et al. |
| 2011/0106146 A1 | 5/2011 | Jeong |
| 2011/0125165 A1 | 5/2011 | Simaan et al. |
| 2011/0152880 A1 | 6/2011 | Alvarez et al. |
| 2011/0160713 A1 | 6/2011 | Neuberger |
| 2011/0167611 A1 | 7/2011 | Williams |
| 2011/0184391 A1* | 7/2011 | Aljuri ................... A61B 18/14 606/2 |
| 2011/0213362 A1 | 9/2011 | Cunningham |
| 2011/0224660 A1 | 9/2011 | Neuberger et al. |
| 2011/0238064 A1 | 9/2011 | Williams et al. |
| 2011/0257641 A1 | 10/2011 | Hastings et al. |
| 2011/0276085 A1 | 11/2011 | Krzyzanowski |
| 2011/0306836 A1 | 12/2011 | Ohline et al. |
| 2011/0313343 A1 | 12/2011 | Milutinovic et al. |
| 2012/0069167 A1 | 3/2012 | Liu et al. |
| 2012/0253277 A1 | 4/2012 | Tah et al. |
| 2012/0138586 A1 | 6/2012 | Webster et al. |
| 2012/0209315 A1 | 8/2012 | Amat |
| 2012/0232342 A1 | 9/2012 | Reydel |
| 2012/0253332 A1 | 10/2012 | Moll |
| 2012/0259320 A1 | 10/2012 | Loesel et al. |
| 2012/0283747 A1 | 11/2012 | Popovic |
| 2012/0296318 A1 | 11/2012 | Wellhofer et al. |
| 2013/0006144 A1 | 1/2013 | Clancy |
| 2013/0035537 A1* | 2/2013 | Wallace ................ A61B 34/30 600/8 |
| 2013/0053877 A1 | 2/2013 | BenMaamer |

(56) References Cited

U.S. PATENT DOCUMENTS

| | | |
|---|---|---|
| 2013/0066136 A1 | 3/2013 | Palese et al. |
| 2013/0085442 A1 | 4/2013 | Shtul et al. |
| 2013/0085486 A1 | 4/2013 | Boutoussov et al. |
| 2013/0096422 A1 | 4/2013 | Boctor |
| 2013/0096574 A1 | 4/2013 | Kang et al. |
| 2013/0110042 A1 | 5/2013 | Humphreys |
| 2013/0110107 A1 | 5/2013 | Smith et al. |
| 2013/0116716 A1 | 5/2013 | Bahls et al. |
| 2013/0144116 A1 | 6/2013 | Cooper et al. |
| 2013/0144274 A1 | 6/2013 | Stefanchik et al. |
| 2013/0144395 A1 | 6/2013 | Stefanchik |
| 2013/0190796 A1 | 7/2013 | Tilson et al. |
| 2013/0225997 A1 | 8/2013 | Dillard et al. |
| 2013/0226161 A1 | 8/2013 | Hickenbotham |
| 2013/0253267 A1 | 9/2013 | Collins |
| 2013/0303876 A1 | 11/2013 | Gelfand et al. |
| 2013/0310819 A1 | 11/2013 | Neuberger et al. |
| 2013/0345686 A1 | 12/2013 | Brown |
| 2014/0005681 A1 | 1/2014 | Gee et al. |
| 2014/0012276 A1 | 1/2014 | Alvarez |
| 2014/0039681 A1 | 2/2014 | Bowling |
| 2014/0046308 A1 | 2/2014 | Bischoff |
| 2014/0051985 A1 | 2/2014 | Fan et al. |
| 2014/0058365 A1 | 2/2014 | Bille |
| 2014/0058404 A1 | 2/2014 | Hammack |
| 2014/0058428 A1 | 2/2014 | Christopher |
| 2014/0100445 A1 | 4/2014 | Stenzel |
| 2014/0142591 A1 | 5/2014 | Alvarez et al. |
| 2014/0163318 A1 | 6/2014 | Swanstrom |
| 2014/0194859 A1 | 7/2014 | Ianchulev |
| 2014/0194905 A1 | 7/2014 | Kappel |
| 2014/0243849 A1 | 8/2014 | Saglam |
| 2014/0275956 A1 | 9/2014 | Fan |
| 2014/0276594 A1 | 9/2014 | Tanner et al. |
| 2014/0276723 A1 | 9/2014 | Parihar |
| 2014/0276956 A1 | 9/2014 | Crainich |
| 2014/0309649 A1 | 10/2014 | Alvarez et al. |
| 2014/0309655 A1 | 10/2014 | Gal et al. |
| 2014/0316203 A1 | 10/2014 | Carroux et al. |
| 2014/0357984 A1 | 12/2014 | Wallace et al. |
| 2014/0364870 A1 | 12/2014 | Alvarez et al. |
| 2015/0051592 A1 | 2/2015 | Kintz |
| 2015/0080879 A1 | 3/2015 | Trees |
| 2015/0119638 A1 | 4/2015 | Yu et al. |
| 2015/0127045 A1 | 5/2015 | Prestel |
| 2015/0133960 A1 | 5/2015 | Lohmeier |
| 2015/0164522 A1 | 6/2015 | Budiman |
| 2015/0164594 A1 | 6/2015 | Romo et al. |
| 2015/0164596 A1 | 6/2015 | Romo |
| 2015/0201917 A1 | 7/2015 | Snow |
| 2015/0202085 A1 | 7/2015 | Lemonis |
| 2015/0314110 A1 | 11/2015 | Park |
| 2015/0335480 A1 | 11/2015 | Alvarez et al. |
| 2016/0001038 A1 | 1/2016 | Romo et al. |
| 2016/0022289 A1 | 1/2016 | Wan |
| 2016/0022466 A1 | 1/2016 | Pedtke |
| 2016/0030073 A1 | 2/2016 | Lsakov |
| 2016/0045208 A1 | 2/2016 | Ciulla |
| 2016/0051318 A1 | 2/2016 | Manzo et al. |
| 2016/0066935 A1 | 3/2016 | Nguyen et al. |
| 2016/0151122 A1 | 6/2016 | Alvarez et al. |
| 2016/0158490 A1 | 6/2016 | Leeflang |
| 2016/0183841 A1 | 6/2016 | Duindam et al. |
| 2016/0199984 A1 | 7/2016 | Lohmeier et al. |
| 2016/0235495 A1 | 8/2016 | Wallace et al. |
| 2016/0249932 A1 | 9/2016 | Rogers et al. |
| 2016/0270865 A1 | 9/2016 | Landey et al. |
| 2016/0279394 A1 | 9/2016 | Moll et al. |
| 2016/0287279 A1 | 10/2016 | Bovay et al. |
| 2016/0303743 A1 | 10/2016 | Rockrohr |
| 2016/0331358 A1 | 11/2016 | Gordon |
| 2016/0367324 A1 | 12/2016 | Sato et al. |
| 2016/0374541 A1 | 12/2016 | Agrawal et al. |
| 2017/0007337 A1 | 1/2017 | Dan |
| 2017/0049471 A1 | 2/2017 | Gaffney et al. |
| 2017/0065227 A1 | 3/2017 | Marrs |
| 2017/0095234 A1 | 4/2017 | Prisco et al. |
| 2017/0095295 A1 | 4/2017 | Overmyer |
| 2017/0100199 A1 | 4/2017 | Yu et al. |
| 2017/0119413 A1 | 5/2017 | Romo |
| 2017/0119481 A1 | 5/2017 | Romo et al. |
| 2017/0135706 A1 | 5/2017 | Frey |
| 2017/0151416 A1 | 6/2017 | Kutikov |
| 2017/0165011 A1 | 6/2017 | Bovay et al. |
| 2017/0172553 A1 | 6/2017 | Chaplin |
| 2017/0172673 A1 | 6/2017 | Yu et al. |
| 2017/0202627 A1 | 7/2017 | Sramek et al. |
| 2017/0209073 A1 | 7/2017 | Sramek et al. |
| 2017/0252096 A1 | 9/2017 | Felder |
| 2017/0265923 A1 | 9/2017 | Privitera |
| 2017/0290631 A1 | 10/2017 | Lee et al. |
| 2017/0319289 A1 | 11/2017 | Neff et al. |
| 2017/0333679 A1 | 11/2017 | Jiang |
| 2017/0340396 A1 | 11/2017 | Romo et al. |
| 2017/0367782 A1 | 12/2017 | Schuh et al. |
| 2018/0000563 A1 | 1/2018 | Shanjani et al. |
| 2018/0025666 A1 | 1/2018 | Ho et al. |
| 2018/0049824 A1 | 2/2018 | Harris |
| 2018/0177383 A1 | 6/2018 | Noonan et al. |
| 2018/0177556 A1 | 6/2018 | Noonan et al. |
| 2018/0193049 A1 | 7/2018 | Heck et al. |
| 2018/0214011 A1 | 8/2018 | Graetzel et al. |
| 2018/0221038 A1 | 8/2018 | Noonan et al. |
| 2018/0221039 A1 | 8/2018 | Shah |
| 2018/0250083 A1 | 9/2018 | Schuh et al. |
| 2018/0271616 A1 | 9/2018 | Schuh et al. |
| 2018/0279852 A1 | 10/2018 | Rafii-Tari et al. |
| 2018/0280660 A1 | 10/2018 | Landey et al. |
| 2018/0289243 A1 | 10/2018 | Landey et al. |
| 2018/0289431 A1 | 10/2018 | Draper et al. |
| 2018/0296285 A1 | 10/2018 | Simi et al. |
| 2018/0325499 A1 | 11/2018 | Landey et al. |
| 2018/0333044 A1 | 11/2018 | Jenkins |
| 2018/0360435 A1 | 12/2018 | Romo |
| 2019/0000559 A1 | 1/2019 | Berman et al. |
| 2019/0000560 A1 | 1/2019 | Berman et al. |
| 2019/0000566 A1 | 1/2019 | Graetzel et al. |
| 2019/0000568 A1 | 1/2019 | Connolly et al. |
| 2019/0000576 A1 | 1/2019 | Mintz et al. |
| 2019/0083183 A1 | 3/2019 | Moll et al. |
| 2019/0099231 A1 | 4/2019 | Bruehwiler |
| 2019/0105776 A1 | 4/2019 | Ho et al. |
| 2019/0105785 A1 | 4/2019 | Meyer |
| 2019/0107454 A1 | 4/2019 | Lin |
| 2019/0110839 A1 | 4/2019 | Rafii-Tari et al. |
| 2019/0110843 A1 | 4/2019 | Ummalaneni et al. |
| 2019/0167366 A1 | 6/2019 | Ummalaneni |
| 2019/0175009 A1 | 6/2019 | Mintz |
| 2019/0175062 A1 | 6/2019 | Rafii-Tari et al. |
| 2019/0175287 A1 | 6/2019 | Hill |
| 2019/0175799 A1 | 6/2019 | Hsu |
| 2019/0183585 A1 | 6/2019 | Rafii-Tari et al. |
| 2019/0183587 A1 | 6/2019 | Rafii-Tari et al. |
| 2019/0216548 A1 | 7/2019 | Ummalaneni |
| 2019/0216576 A1 | 7/2019 | Eyre |
| 2019/0223974 A1 | 7/2019 | Romo |
| 2019/0228525 A1 | 7/2019 | Mintz et al. |
| 2019/0239890 A1 | 8/2019 | Stokes |
| 2019/0246882 A1 | 8/2019 | Graetzel et al. |
| 2019/0262086 A1 | 8/2019 | Connolly et al. |
| 2019/0269468 A1 | 9/2019 | Hsu et al. |
| 2019/0274764 A1 | 9/2019 | Romo |
| 2019/0290109 A1 | 9/2019 | Agrawal et al. |
| 2019/0298160 A1 | 10/2019 | Ummalaneni et al. |
| 2019/0298460 A1 | 10/2019 | Al-Jadda |
| 2019/0298465 A1 | 10/2019 | Chin |
| 2019/0314616 A1 | 10/2019 | Moll et al. |
| 2019/0328213 A1 | 10/2019 | Landey et al. |
| 2019/0336238 A1 | 11/2019 | Yu |
| 2019/0365209 A1 | 12/2019 | Ye et al. |
| 2019/0365479 A1 | 12/2019 | Rafii-Tari |
| 2019/0365486 A1 | 12/2019 | Srinivasan et al. |
| 2019/0374297 A1 | 12/2019 | Wallace et al. |
| 2019/0375383 A1 | 12/2019 | Alvarez |

(56) References Cited

U.S. PATENT DOCUMENTS

| | | |
|---|---|---|
| 2019/0380787 A1 | 12/2019 | Ye |
| 2019/0380797 A1 | 12/2019 | Yu |
| 2020/0000530 A1 | 1/2020 | DeFonzo |
| 2020/0000533 A1 | 1/2020 | Schuh |
| 2020/0022767 A1 | 1/2020 | Hill |
| 2020/0039086 A1 | 2/2020 | Meyer |
| 2020/0046434 A1 | 2/2020 | Graetzel |
| 2020/0054408 A1 | 2/2020 | Schuh |
| 2020/0060516 A1 | 2/2020 | Baez |
| 2020/0093549 A1 | 3/2020 | Chin |
| 2020/0093554 A1 | 3/2020 | Schuh |
| 2020/0100845 A1 | 4/2020 | Julian |
| 2020/0100853 A1 | 4/2020 | Ho |
| 2020/0100855 A1 | 4/2020 | Leparmentier |
| 2020/0101264 A1 | 4/2020 | Jiang |
| 2020/0107894 A1 | 4/2020 | Wallace |
| 2020/0121502 A1 | 4/2020 | Kintz |
| 2020/0146769 A1 | 5/2020 | Eyre |
| 2020/0163726 A1 | 5/2020 | Tanner |

FOREIGN PATENT DOCUMENTS

| | | |
|---|---|---|
| CN | 103298414 | 9/2013 |
| CN | 205729413 | 11/2016 |
| EP | 1 321 106 | 6/2003 |
| EP | 1 849 423 | 10/2007 |
| JP | 09-224951 | 9/1997 |
| JP | 2005-270464 | 10/2005 |
| WO | WO 03/096871 | 11/2003 |
| WO | WO 04/105849 | 12/2004 |
| WO | WO 11/161218 | 12/2011 |
| WO | WO 13/107468 | 7/2013 |
| WO | WO 13/130895 | 9/2013 |
| WO | WO 17/114855 | 7/2017 |
| WO | WO 18/069679 | 4/2018 |

OTHER PUBLICATIONS

Ehlers, et al. Integration of a spectral domain optical coherence tomography system into a surgical microscope for intraoperative imaging. Investigative Ophthalmology and Visual Science 52.6. 2011; 3153-3159.

Hubschman. Robotic Eye Surgery: Past, Present, and Future. Journal of Computer Science and Systems Biology. 2012.

Stoyanov, Oct. 20, 2011, Surgical Vision, Annals of Biomedical Engineering 40(2):332-345.

Verdaasdonk et al., Jan. 23, 2012, Effect of microsecond pulse length and tip shape on explosive bubble formation of 2.78 μm Er,Cr;Ysgg and 2.94 μm Er:YAG laser, Proceedings of SPIE, vol. 8221; 12.

European search report and search opinion dated Jul. 2, 2015 for EP Application No. 12856685.8.

International search report dated Jun. 16, 2014 for PCT/US2014/022424.

International search report and written opinion dated Mar. 29, 2013 for PCT/US2012/069540.

International search report and written opinion dated Jan. 27, 2015 for PCT Application No. PCT/US2014/062284.

International Search Report dated Nov. 7, 2014 in PCT/US2014/041990.

\* cited by examiner

106

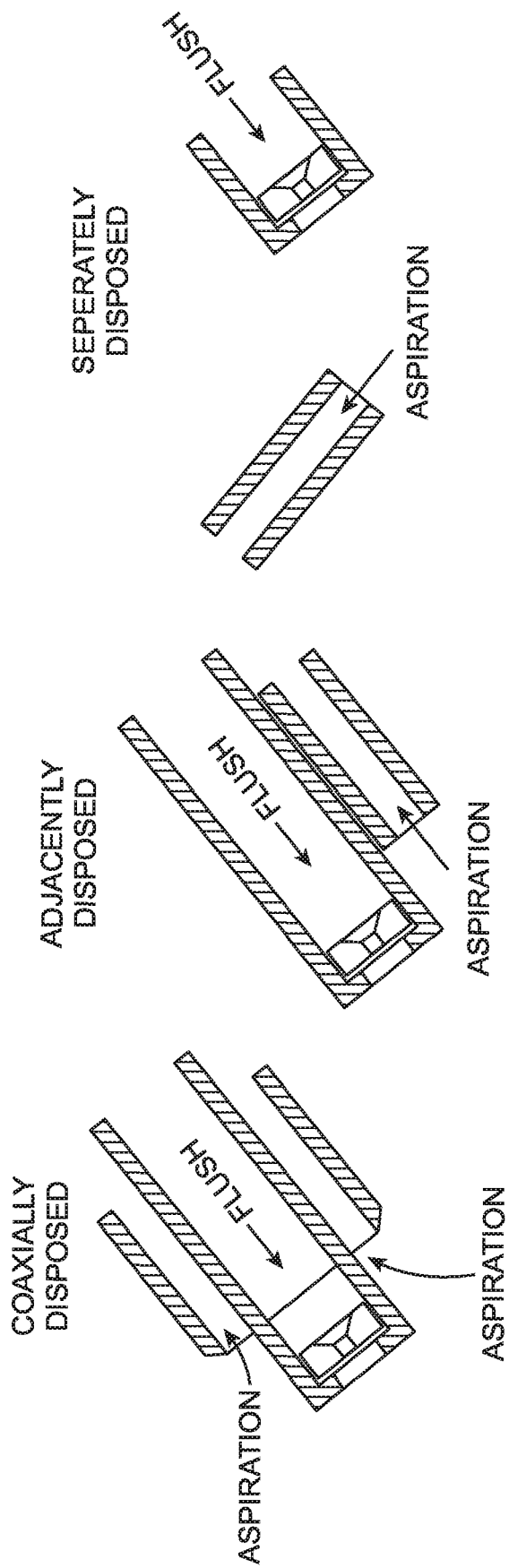

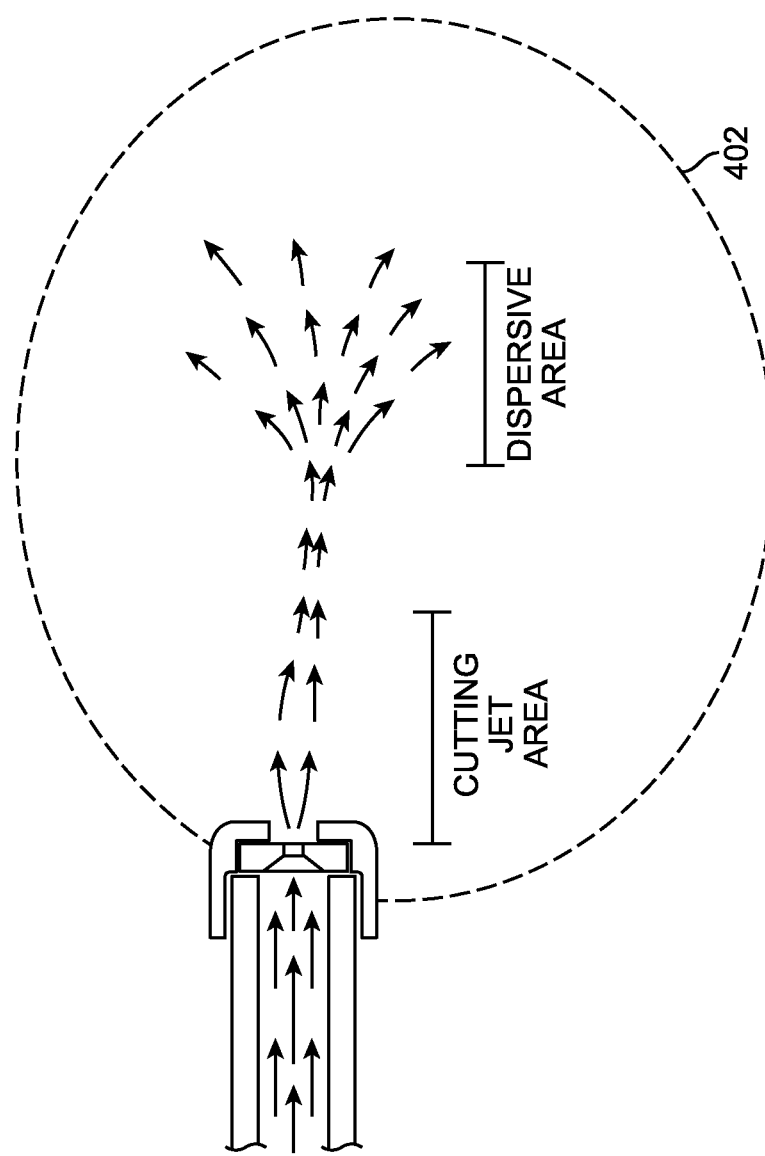

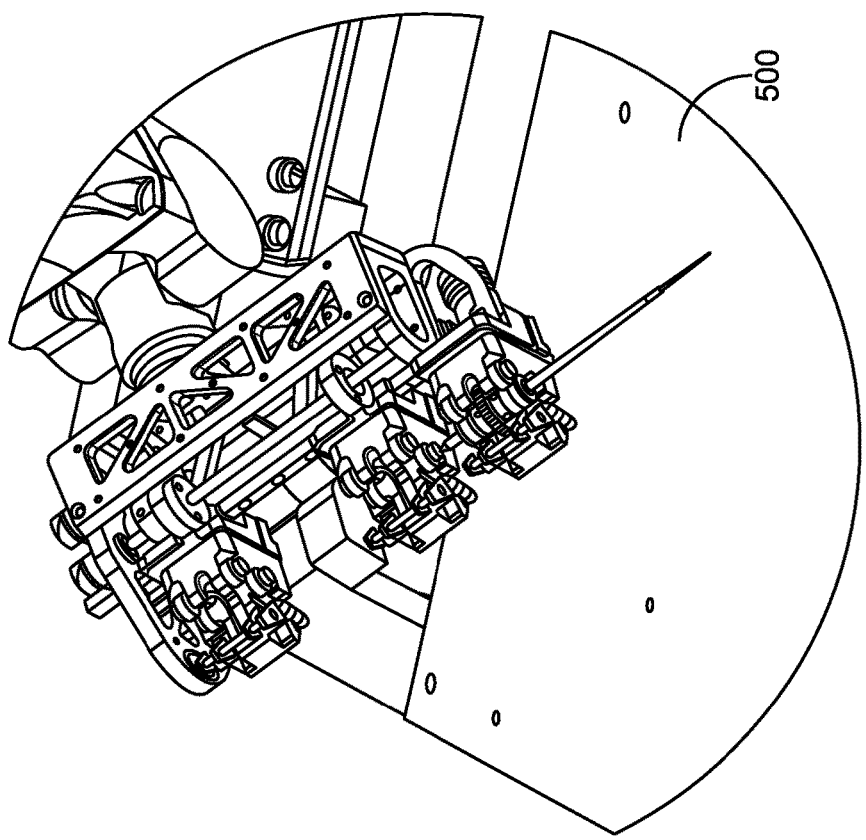
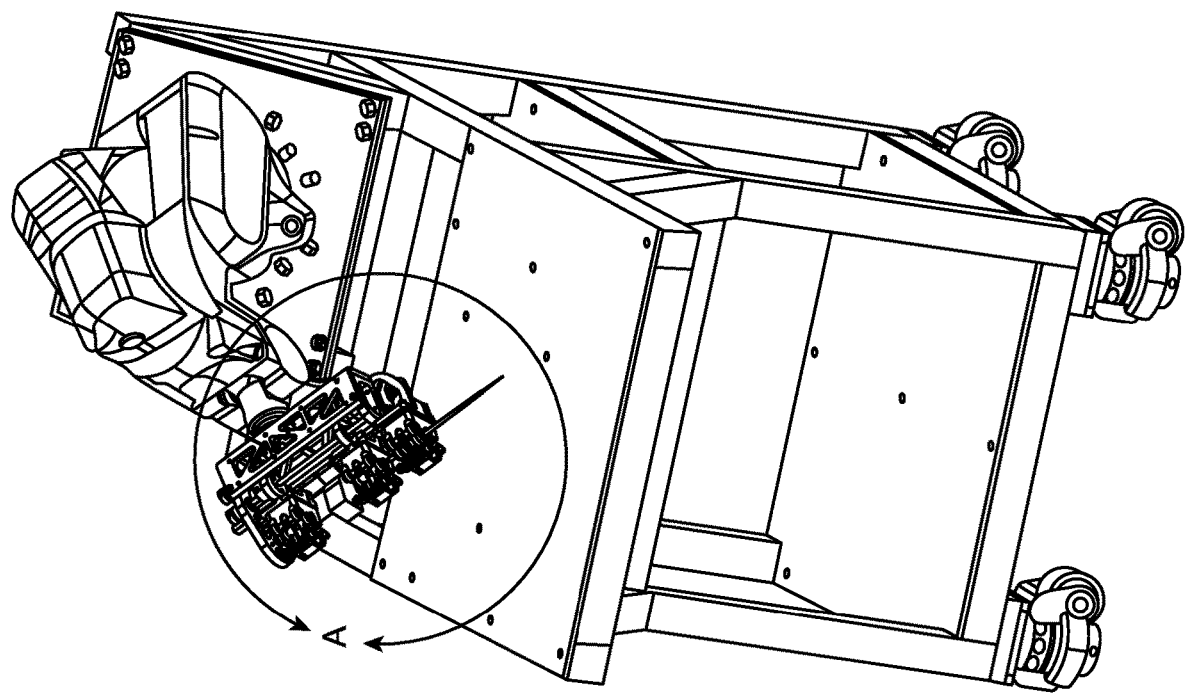
FIG. 5

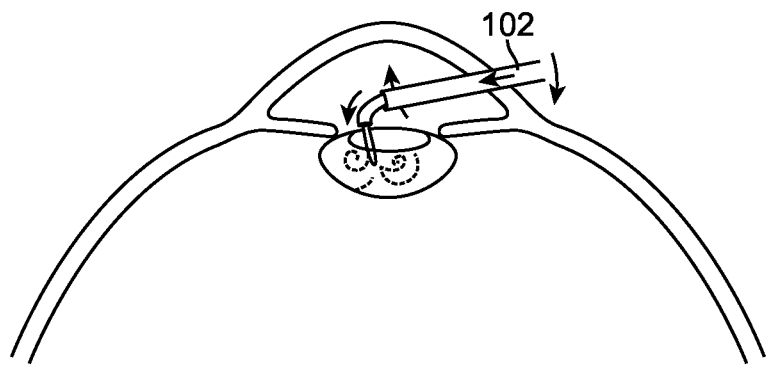
TOP VIEW
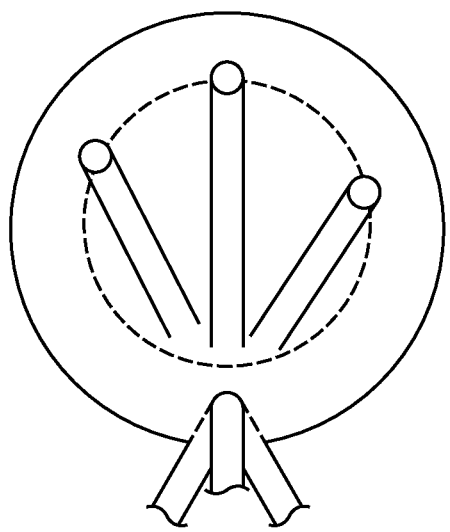
FIG. 7E

METHOD, APPARATUS AND SYSTEM FOR A WATER JET

CROSS-REFERENCE TO RELATED APPLICATIONS

This application is a continuation of U.S. patent application Ser. No. 14/158,548 filed Jan. 17, 2014, which claims the benefit of U.S. Provisional Application No. 61/754,426, filed Jan. 18, 2013, the entire contents of which are incorporated herein by reference in their entirety.

BACKGROUND OF THE INVENTION

1. Field of the Invention

The field of the present application pertains to medical devices. More particularly, the field of the invention pertains to an apparatus, system, and method for performing surgery.

2. Description of the Background Art

A cataract is a clouding of the lens in the eye that affects vision. Most cataracts are related to aging. Cataracts are very common in older people. By age 80, more than half of all Americans either have a cataract or have had cataract surgery.

The lens lies behind the iris and the pupil. It works much like a camera lens. It focuses light onto the retina at the back of the eye, where an image is recorded. The lens also adjusts the eye's focus, letting us see things clearly both up close and far away. The lens is made of mostly water and protein. The protein is arranged in a precise way that keeps the lens clear and lets light pass through it. But as we age, some of the protein may clump together and start to cloud a small area of the lens. This is a cataract. Over time, the cataract may grow larger and cloud more of the lens, making it harder to see.

Age-related cataracts can affect vision in two ways. First, clumps of protein reduce the sharpness of the image reaching the retina. The lens consists mostly of water and protein. When the protein clumps up, it clouds the lens and reduces the light that reaches the retina. The clouding may become severe enough to cause blurred vision. Most age-related cataracts develop from protein clumping. Second, the clear lens slowly changes to a yellowish/brownish color, adding a brownish tint to vision. As the clear lens slowly colors with age, it may gradually cause vision to have a brownish shade. At first, the amount of tinting may be small and may not cause a vision problem. Over time, increased tinting may make it more difficult to read and perform other routine activities.

Surgery is the only real treatment for cataracts. Each year, cataract surgeons in the United States perform over three million cataract surgeries. One of the more conventional cataract surgery procedures is called extracapsular cataract extraction (ECCE). Extracapsular cataract extraction involves the removal of almost the entire natural lens while the elastic lens capsule (posterior capsule) is left intact to allow implantation of an intraocular lens. It involves manual expression of the lens through a large (usually 10-12 mm) incision made in the cornea or sclera. Although it requires a larger incision and the use of stitches, the conventional method may be indicated for patients with very hard cataracts or other situations in which phacoemulsification is problematic.

Modern cataract surgery is usually performed using a microsurgical technique called phacoemulsification, whereby the cataract is emulsified with an ultrasonic handpiece and then suctioned out of the eye. Before phacoemulsification can be performed, one or more incisions are made in the eye to allow the introduction of surgical instruments. The surgeon then removes the anterior face of the capsule that contains the lens inside the eye. A phacoemulsification probe is an ultrasonic handpiece with a titanium or steel needle. The tip of the needle vibrates at ultrasonic frequency to sculpt and emulsify the cataract while a pump aspirates particles through the tip. In some techniques, a second fine steel instrument called a chopper is used from a side port to help with chopping the nucleus into smaller pieces. The cataract is usually broken into two or four pieces and each piece is emulsified and aspirated out with suction. The nucleus emulsification makes it easier to aspirate the particles. After removing all hard central lens nucleus with phacoemulsification, the softer outer lens cortex is removed with suction only. As with other cataract extraction procedures, an intraocular lens implant (IOL), is placed into the remaining lens capsule.

One possible improvement to phacoemulsification is a cataract surgery performed with lasers. Femtosecond Laser cataract surgery is rapidly emerging as a potential technology that may allow for improved precision of incision formation and emulsification of the cataract.

Although phacoemulsification and laser-based cataract surgery work well for many patients, these technologies have several shortcomings. For example, phacoemulsification ultrasound probes must propagate ultrasound energy along the length of the probe, from a proximal transducer to a distal tip. This propagation may lead to transmission of ultrasound energy along the probe to tissues in and around the eye that do not benefit from the transmission. Ultrasound probes also tend to generate more heat than would be desirable for a procedure in the eye. Finally, it may be quite difficult to steer an ultrasound probe around corners or bends, due to the mechanical requirements of propagating the ultrasound wave along the entire instrument. In other words, the probe may have to be rigid or at least more rigid than would be desirable.

Probe based lasers have similar drawbacks. They may generate unwanted heat in the eye and are often difficult to control, thus risking damage to important nearby tissues. They also are easily damaged when attempting to navigate tight corners, as fibers in a laser probe may easily break. Femtosecond laser systems are costly to own and operate and have the additional drawback of extending operative time.

Therefore, it would be advantageous to have a method and device for treating cataracts, and potentially other eye ailments, that included many of the advantages of phacoemulsification and laser procedures without at least some of the drawbacks. Ideally, such a method and device would be relatively simple to manufacture and implement, and would work well for performing cataract surgery without harming surrounding eye tissue. Also ideally, the method and/or device would be applicable to one or more other eye conditions.

Many people worldwide are afflicted by chronic or acute intermittent sinusitis, and it can often be a debilitating disease that affects one's ability to exercise, breathe, fly on airplanes, and the like. Chronic or acute intermittent sinusitis sufferers often experience symptoms such as drainage of a thick, yellow or greenish discharge from the nose or down the back of the throat, nasal obstruction or congestion, causing difficulty breathing through your nose, pain, tenderness and swelling around the eyes, cheeks, nose or forehead, reduced sense of smell and taste, ear pain, aching in the upper jaw and teeth, cough, which may be worse at night, sore throat, bad breath (halitosis), fatigue or irritability and nausea. Several types of surgical procedures have been developed to treat chronic sinusitis, such as functional endoscopic sinus surgery ("FESS") and balloon sinuplasty. FESS is very invasive, however, and requires a long and painful recovery process. Balloon sinuplasty is less invasive but is not effective in all patients.

Some existing solutions are discussed in several issued patents and publications. For example, U.S. Pat. No. 7,967,799 teaches a liquefaction hand-piece tip. However, the tip requires a standoff or spacer to keep the distal end from directly contacting delicate tissue. In another existing solution, United States publication 2004/0030349 creates pulses of fluid. However, the fluid needs to be heated.

Therefore, it would be beneficial to have a new method, apparatus, and system for performing surgery for various applications including eye, micro-surgery, and/or other emulsification applications.

SUMMARY OF THE INVENTION

Embodiments described herein are directed to a method, apparatus, and system for performing surgery for various applications including eye, micro-surgery, and/or other emulsification applications. Specifically, in one embodiment, a water jet apparatus may be used for manually performing eye surgery such as, cataract, or perform microsurgery (remove cartilage), endoscopic orthopedic surgery, surgery of the ear, or any other procedure requiring removal of tissue in a small confined space. In other embodiments, a system with robotic control of the water jet apparatus may be used. In these embodiments, the water jet apparatus is coupled to a robotic arm via an instrument drive mechanism.

In other embodiments, methods and workflows for cataract extraction are discussed to facilitate the use of the previous apparatus and system embodiments. For example, the workflows depicted are efficient and replace typical steps in a common modern cataract extraction flow. For example, the traditional Hydro dissection, Nuclear fracture, and emsulfication steps are replaced with a single water jet emulsification step.

In another aspect of the present invention, a method of utilizing the water jet apparatus treating a cataract in an eye may involve controlling a cutting jet area of the water jet based at least in part on a flow rate meter utilizing a feedback loop to a pump.

In another aspect of the present invention, the water jet apparatus utilizes a nozzle that has a jet cutting area and a dispersive area. In one embodiment, the water jet apparatus could be coupled to a system that incorporates a flow rate meter or pressure gauge, pressure vessel or reservoir, and pump. A feedback loop from the flow meter to the pump is controlled by a computer, central processing unit, microcontroller, or any custom application specific integrated circuit (ASIC). In another embodiment, a feedback loop exists at the aspiration pump that is controlled by a computer, central processing unit, microcontroller, or any custom application specific integrated circuit (ASIC). In yet another embodiment, a throttle valve helps to control the flow rate meter based on a feedback loop. All the previous embodiments are discussed in different versions of FIGS. 3A, B, C, and D.

These and other aspects and embodiments will be described in greater detail below, in reference to the attached drawing figures.

BRIEF DESCRIPTION OF THE DRAWINGS

FIGS. 3A, 3B, 3C, 3D, 3E, 3F, and 3G are block diagrams of a water jet system, according to multiple embodiments of the present invention;

FIG. 4 is a cross section side view of an output of the nozzle with a cutting jet area and dispersive area depicted, according to another embodiment of the present invention;

FIG. 5 is an instrument drive mechanism to couple the water jet to a robotic system, according to another embodiment of the present invention;

FIGS. 7A-7G are side, cross-sectional views of a portion of an eye, illustrating a method for using the water jet apparatus to perform cataract surgery, according to one embodiment of the present invention;

DETAILED DESCRIPTION OF THE PREFERRED EMBODIMENT

Figure 1:
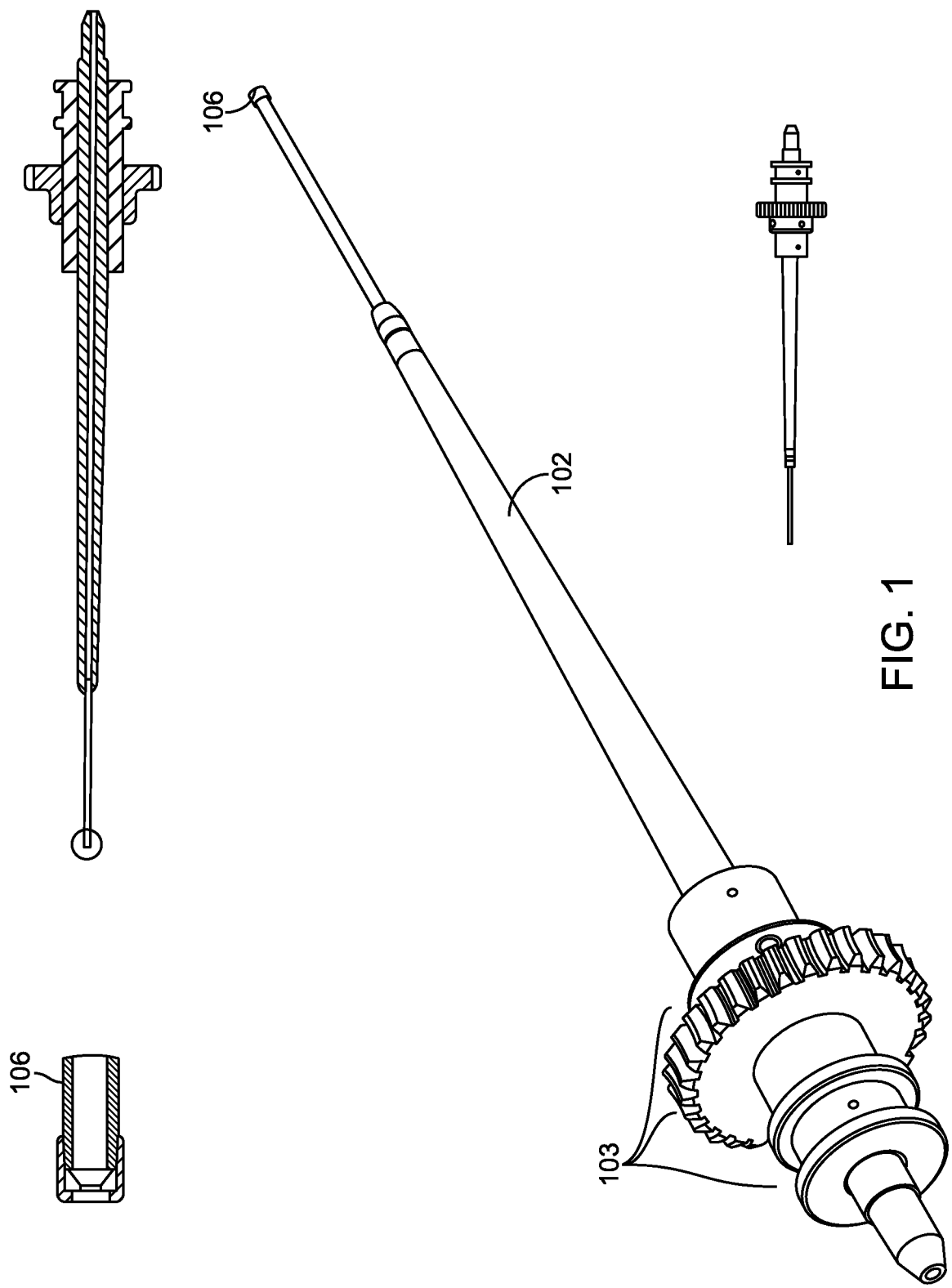
FIG. 1 is a perspective view of a water jet apparatus, according to one embodiment of the present invention.

Although certain preferred embodiments and examples are disclosed below, inventive subject matter extends beyond the specifically disclosed embodiments to other alternative embodiments and/or uses, and to modifications and equivalents thereof. Thus, the scope of the claims appended hereto is not limited by any of the particular embodiments described below. For example, in any method or process disclosed herein, the acts or operations of the method or process may be performed in any suitable sequence and are not necessarily limited to any particular disclosed sequence. Various operations may be described as multiple discrete operations in turn, in a manner that may be helpful in understanding certain embodiments; however, the order of description should not be construed to imply that these operations are order dependent. Additionally, the structures, systems, and/or devices described herein may be embodied as integrated components or as separate components.

For purposes of comparing various embodiments, certain aspects and advantages of these embodiments are described. Not necessarily all such aspects or advantages are achieved by any particular embodiment. Thus, for example, various embodiments may be carried out in a manner that achieves or optimizes one advantage or group of advantages as taught herein without necessarily achieving other aspects or advantages as may also be taught or suggested herein.

The embodiments described herein are directed to method, apparatus, and system for performing surgery for various applications including eye, micro-surgery, and/or other emulsification applications. Specifically, in one embodiment, a water jet apparatus may be used for manually performing eye surgery such as, cataract, or perform microsurgery (remove cartilage), or any emulsification technique. In the case of a cataract in an eye, a water jet apparatus or system may be used to break apart a cataract into multiple, smaller pieces, which may then be suctioned from the eye using the probe or other suction means. Although the method and device are typically described below in the context of treating cataracts, in various alternative embodiments, other eye conditions may be treated.

In other embodiments, a system with robotic control of the water jet apparatus may be used. In these embodiments, the water jet apparatus is coupled to a robotic arm via an instrument drive mechanism, depicted in connection with FIG. 5. It may be advantageous to incorporate any of the water jet apparatus or water jet system described herein into a robotic surgery/delivery system, such as, the system depicted in FIG. 6. For example, any of the water jet apparatus or water jet systems may be incorporated into the da Vinci® Surgical System, provided by Intuitive Surgical, Inc., or the Magellan™ Robotic System, provided by Hansen Medical, Inc. the RiO, provided by Mako Surgical or Carnegie Mellon's Micron, or John Hopkins University's Steady Hand. Robotic surgical systems such as (but not limited to) these examples may register the water jet apparatus to the target anatomy. Such capability enables both precise and safe movement water jet apparatus such that, when enabled, the fluid is focused in the desired jet cutting area and rapidly dispersed outside of that in order to treat the target tissue and spares injury to surrounding tissue. A number of robotic surgery systems are presently known, and others may be developed specifically for use with the water jet probes and methods described herein.

In other embodiments, methods and workflows for cataract extraction are discussed to facilitate the use of the previous apparatus and system embodiments. For example, the workflows depicted are efficient and replace typical steps in a common modern cataract extraction flow. For example, the common Hydro dissection, Nuclear fracture, and emulsification steps are replaced with a single water jet emsulfication step. The improved workflows are depicted in connection with FIGS. 9-11.

In another aspect of the present invention, a method of utilizing the water jet apparatus treating a cataract in an eye may involve controlling a cutting jet area of the water jet based at least in part on a flow rate meter utilizing a feedback loop to a pump, as depicted in connection with FIG. 3.

In another aspect of the present invention, the water jet apparatus utilizes a nozzle that generates a jet cutting area and a dispersive area when pressurized water is passed through it into a fluid filled environment, a preferred embodiment uses saline. In one embodiment, the water jet apparatus could be coupled to a system that incorporates a flow rate meter, pressure vessel, and pump. A feedback loop from the flow meter to the pump is controlled by a computer or central processing unit, as depicted in connection with FIG. 3A.

Figure 2:
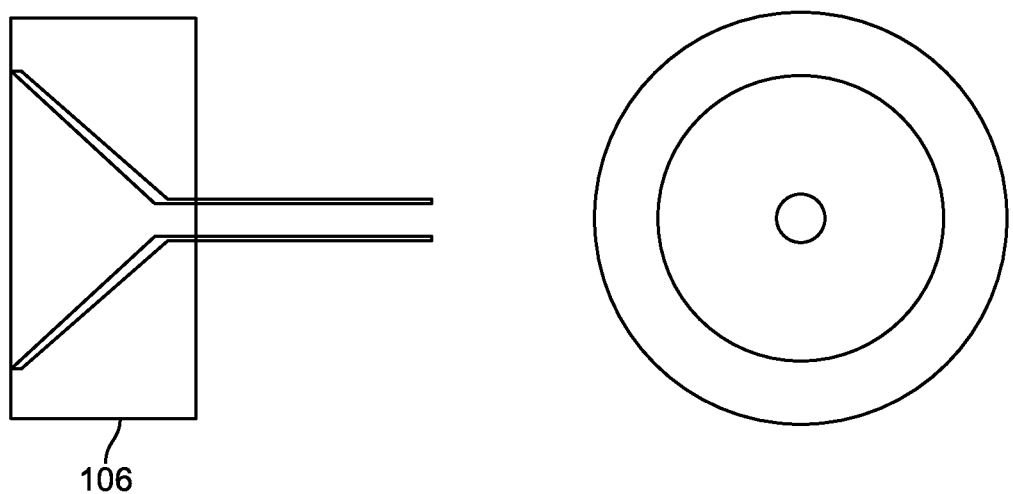
FIG. 2 is a side-view of a portion of a nozzle of the water jet apparatus depicted in FIG. 1.

Referring to FIGS. 1 and 2, one embodiment of a water jet apparatus 102 includes a tip with a nozzle 106 at a distal end and a instrument drive coupling mechanism 103 at a proximal end. The nozzle 106 is depicted in further detail in FIG. 2. In one embodiment, the instrument drive coupling mechanism 103 facilitates coupling to a instrument drive mechanism as depicted in connection with FIG. 5. For this embodiment, the apparatus may be controlled by a robotic system as depicted in connection with FIG. 6 or the previous embodiments depicted in connection with da Vinci® Surgical System, provided by Intuitive Surgical, Inc., or the Magellan™ Robotic System, provided by Hansen Medical, Inc., or Carnegie Mellon's Micron, or John Hopkins University's Steady Hand.

However, in another embodiment, the water jet apparatus 102 would not have a instrument drive coupling mechanism 103 and would be used in a manual and may have a different configuration at the proximal end.

In one embodiment, the water jet apparatus would consist of the probe 102. In another embodiment, the water jet apparatus could be configured to include or support the other block diagrams depicted in connection with FIGS. 3A, B, C, and D.

Referring to FIG. 2, a side-view a portion of a nozzle 106 of the water jet apparatus is depicted. In one embodiment, the nozzle 106 is a sapphire orifice manufactured by Swiss Jewel Company. In this embodiment, the nozzle 106 may have a plurality of different diameter measurements, thickness, angle, and Vee depth as depicted in the table in connection with FIG. 2. However, the claimed subject matter is not limited to neither the different measurements depicted nor configurations implied by the illustration. For instance one skilled in the art appreciates utilizing different measurements or configurations as needed for the particular application or other factors, such as, jet cutting area, dispersive area, pressure levels, exiting location or nozzle orientation.

However, the claimed subject matter is not limited to a sapphire orifice nozzle. One skilled in the art appreciates utilizing not only different nozzle configurations, but also different nozzle material, such as, but not limited to, diamond or stainless steel.

Figure 3A:
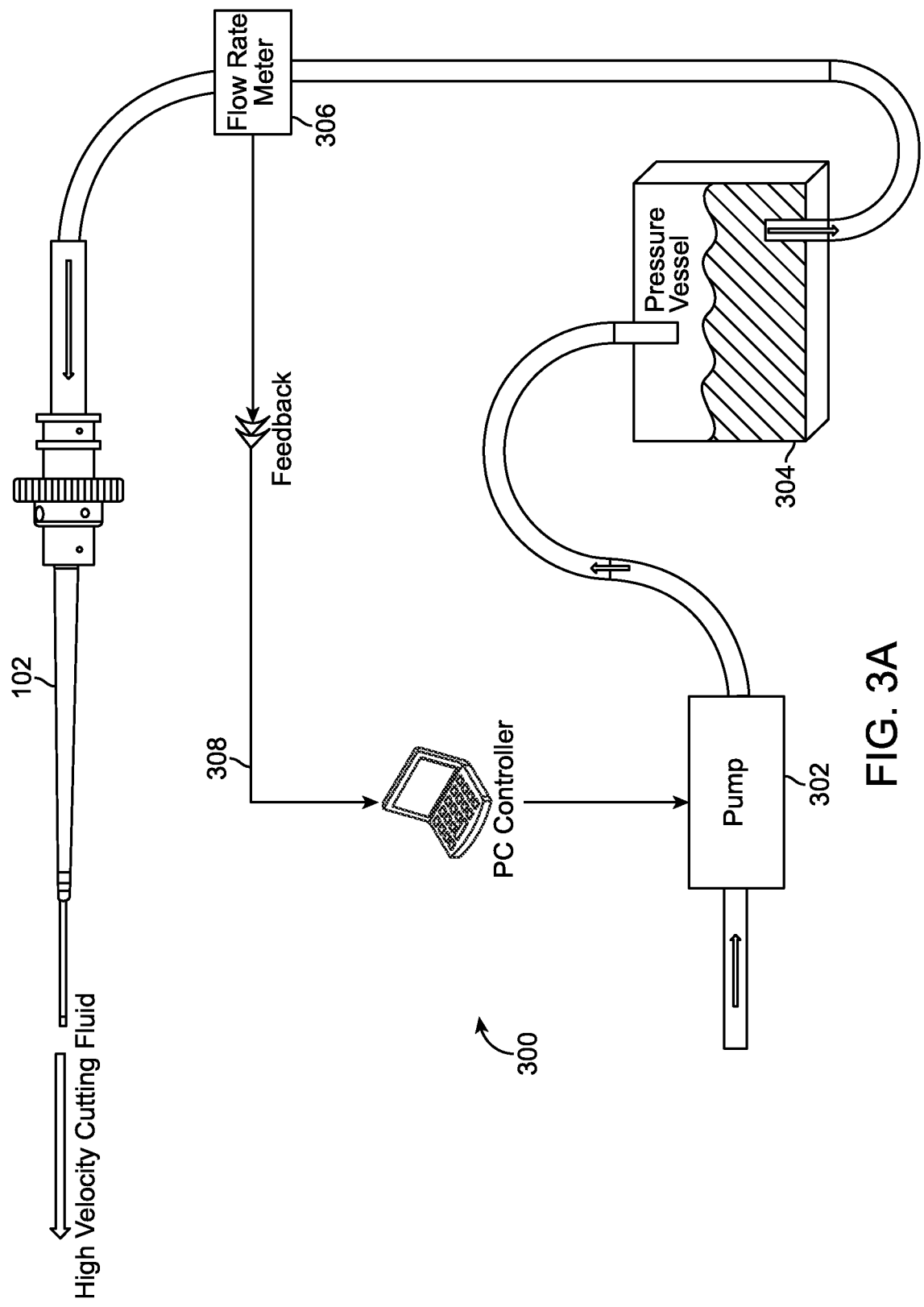

Referring to FIG. 3A, a block diagram of a water jet system 300 is depicted. As discussed earlier, the water jet apparatus 102 of FIG. 1 may incorporate or be coupled to block diagrams depicted in connection with FIGS. 3A, B, C, and D, such as, a pump, pressure vessel, throttle valve, aspiration pump, and flow rate meter.

In one embodiment for a robotic control system, the water jet apparatus 102 is controlled by a robotic system, because the water jet apparatus is coupled to an instrument drive mechanism. For this embodiment, the other blocks depicted, such as, flow rate meter, computer, feedback loop, pump, and pressure vessel, are coupled to the robotic arm while residing near the robotic arm.

In another embodiment, the water jet apparatus 102 includes a pressure vessel, and is controlled by a robotic system, because the water jet apparatus is coupled to an instrument drive mechanism. For this embodiment, the other blocks depicted, such as, flow rate meter, personal computer, feedback loop, and pump are coupled to the robotic arm while residing near the robotic arm.

In yet another embodiment, the water jet apparatus 102 is manually controlled and may be coupled to the other block diagrams via an interface.

In this water jet system 300, the fluid enters a pump 302 and is forwarded to a pressure vessel 304 via a tube. An output of the pressure vessel is forwarded to the flow rate meter 306. In one embodiment, an output of the flow rate meter is controlled by a feedback loop through a computer and a pump. The feedback loop facilitates the output of the flow rate meter based on a desired jet cutting area of an output of the nozzle 106 from the water jet apparatus.

Figure 3B:
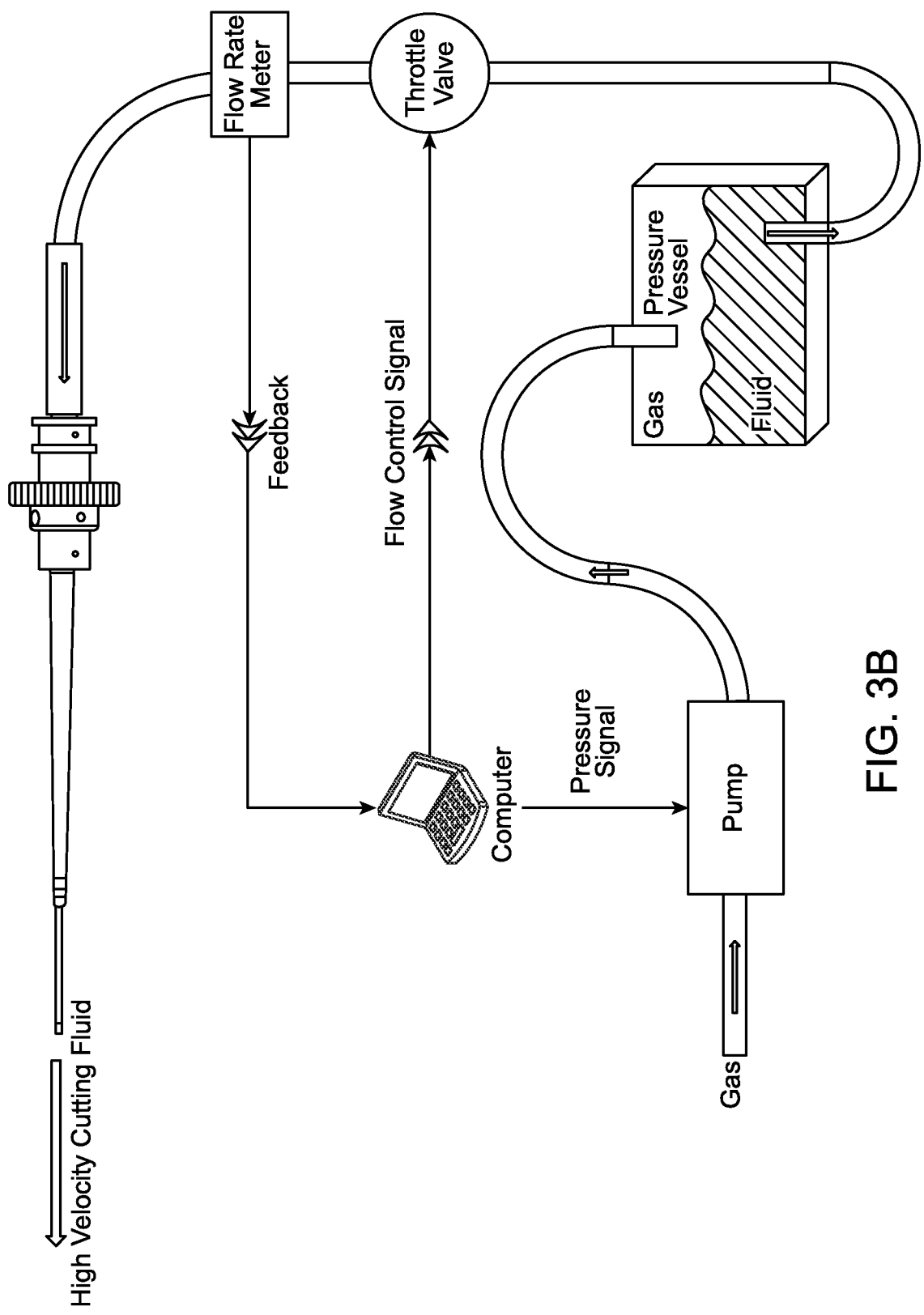
Figure 3C:
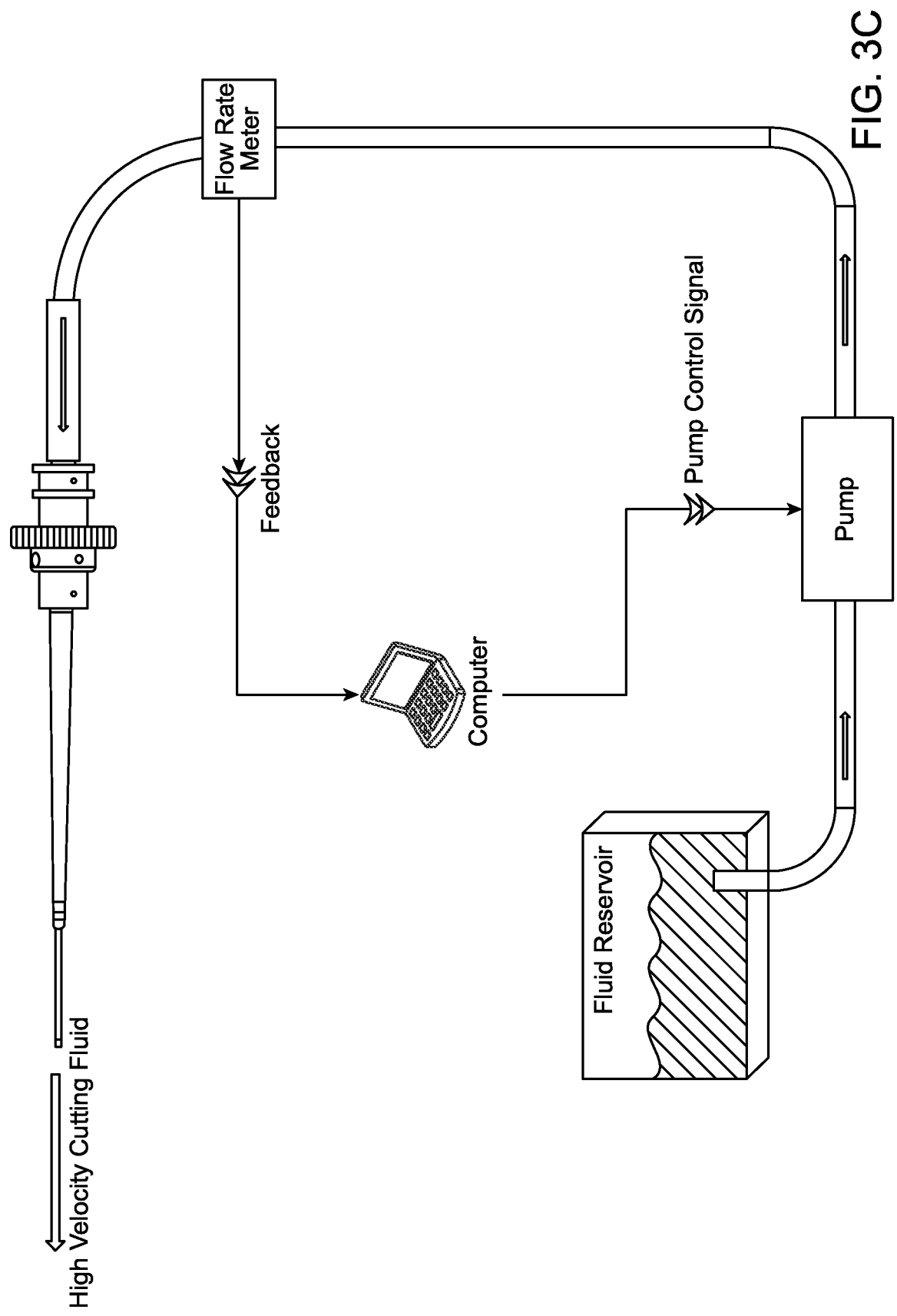

In alternative embodiments, FIG. 3B depicts a throttle valve to help facilitate the flow rate based on a feedback loop. In this embodiment, the throttle valve receives the control signal from either a computer, central processing unit, microcontroller, ASIC, or other control circuitry. In yet another embodiment, FIG. 3C depicts a fluid reservoir coupled to the pump, wherein the feedback loop between the flow rate meter and pump is controlled by a computer, central processing unit, microcontroller, ASIC, or other control circuitry.

Figure 3D:
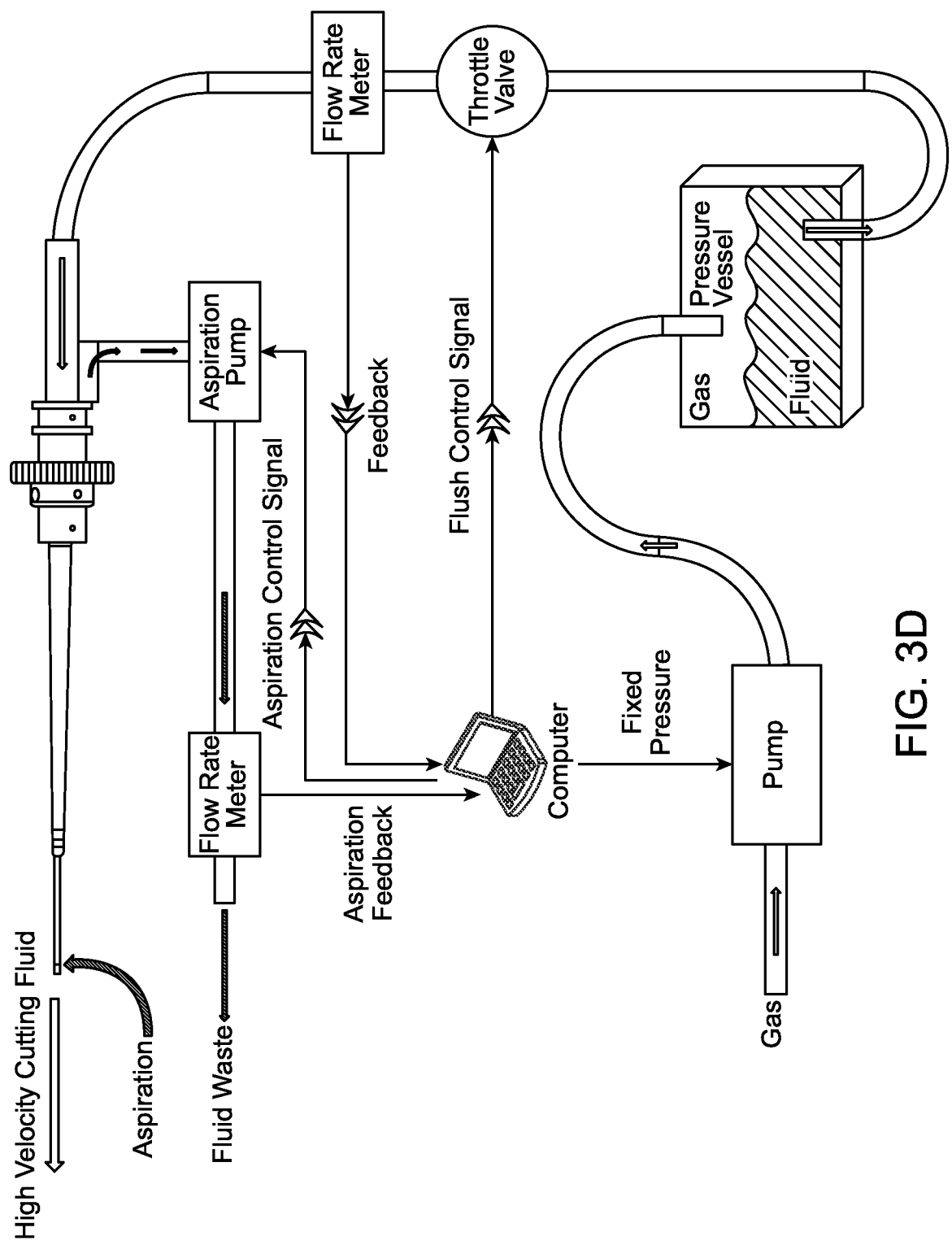

In yet another embodiment, FIG. 3D depicts an aspiration pump that controls removal of material from the operative site. It also has a feedback loop with a flow rate meter that is controlled by a computer, central processing unit, microcontroller, ASIC, or other control circuitry. The aspiration pump may be controlled by the Aspiration flow rate meter feedback signal and or the water jet flow rate meter feedback signal to maintain a desired absolute aspiration flow, or to track the water jet flow in order to maintain the material volume in an enclosed operative space like the interior of the eye. Similarly in this configuration the Water Jet flow may be moderated or interrupted automatically, using the throttle valve or pump control, based on the measured aspiration flow. This may be done in the event that the aspiration path is unable to match the desired flow rate due to blockage, pinched tube, or other mechanical failure.

Referring to FIGS. 3E-3G, multiple embodiments of water jet system configurations are depicted. The configuration on of FIG. 3E depicts a coaxially disposed configuration of a water jet fluid flush with an aspiration on either side. The configuration of FIG. 3F depicts an adjacently disposed water jet fluid flush and aspiration in a separate tube. In the embodiment of FIG. 3G, the water jet fluid flush and aspiration are separately disposed.

Referring to FIG. 4, a fluid output of the nozzle 106 is depicted as first a focused cutting jet area and eventually a dispersive area. In one embodiment, the cutting jet area and dispersive area are in a fluid medium 402, such as, a saline solution. As mentioned in connection with FIGS. 3A, B, C, and D, the feedback loops control the flow of fluid to the water jet apparatus 102. For example, if the jet cutting area needs to be increased, the flow rate meter could request an increase in pressure from the pump. Alternatively, if the jet cutting area needs to be decreased, the flow rate meter could request an decrease in pressure from the pump.

Referring to FIG. 5, an instrument drive mechanism to couple the water jet to a robotic system is depicted. In one embodiment, the instrument drive coupling mechanism 103 of FIG. 1 is used to facilitate coupling to the instrument drive mechanism depicted in FIG. 5. For this embodiment, the apparatus may be controlled by a robotic system as depicted in connection with FIG. 6 or the previous embodiments depicted in connection with da Vinci® Surgical System, provided by Intuitive Surgical, Inc., or the Magellan™ Robotic System, provided by Hansen Medical, Inc., or Carnegie Mellon's Micron, or John Hopkins University's Steady Hand.

However, the instrument drive mechanism is not limited to this embodiment. One skilled in the art appreciates modifications to facilitate coupling to different robotic arm configurations.

Figure 6:
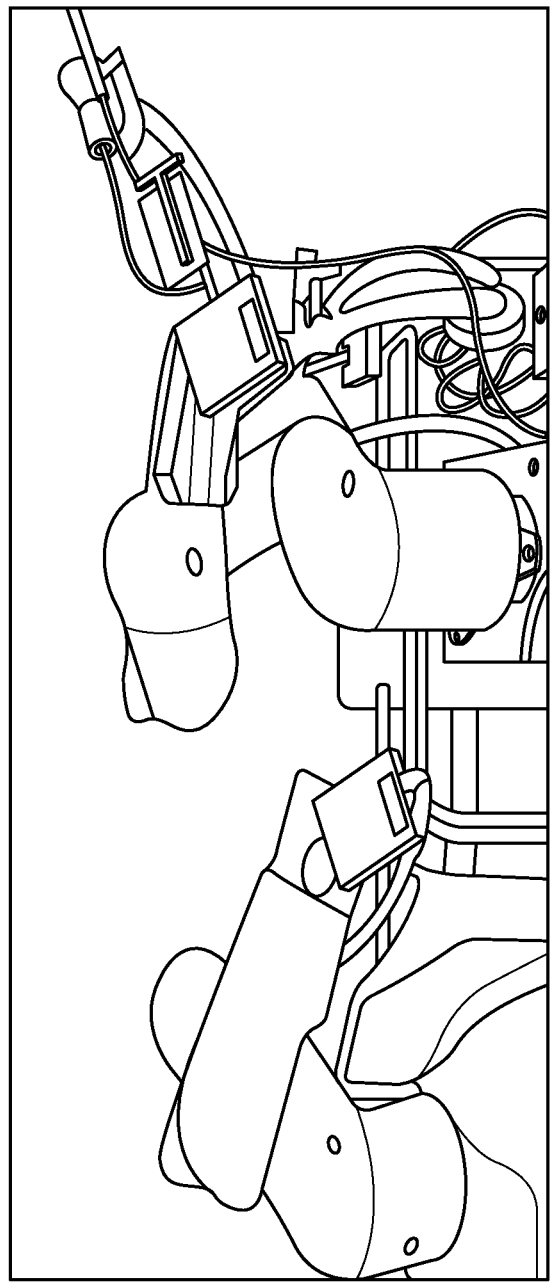
FIG. 6 is a robotic system to control the water jet apparatus or water jet system, according to another embodiment of the present invention.

FIG. 6 is a robotic system to control the water jet apparatus or water jet system. As discussed earlier, the instrument drive mechanism described in FIG. 5 may be used to couple the water jet apparatus or system to facilitate control by this robotic system configuration.

In this embodiment for a robotic control system, two instrument drivers each of which contains an instrument interface that drives a medical instrument is depicted. However, the claimed subject matter is not limited to this particular robotic system and could support any robotic control system with one or more interfaces and one or more instrument drivers. As previously mentioned, various robotic systems facilitate control of the water jet apparatus within the eye. For example, the robotic systems could utilize known localization techniques, such as, 3D imaging, MRI, CT, Ultrasound, Intra operative (OCT), and the like.

Turning now to FIGS. 7A-7G, one embodiment of a method for treating a cataract is illustrated. For convenience, only a distal portion of the probe 102 is illustrated in these figures. Also, in various alternative embodiments of the method, the water jet 102 may either manual or coupled with a robotic surgery system. Thus, the present description may be applied to any delivery method, whether robotic or not. Any suitable imaging system may be incorporated as well, sometimes as part of the robotic system. Three dimensional imaging is but one example.

Figure 7A:
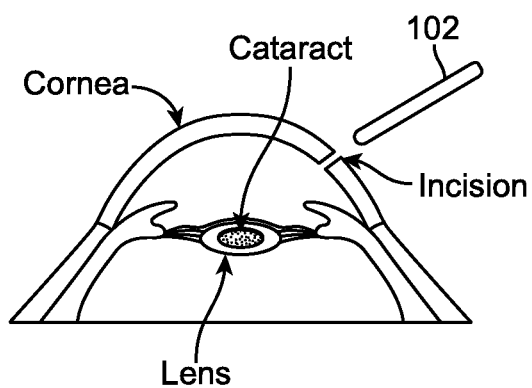
Figure 7B:
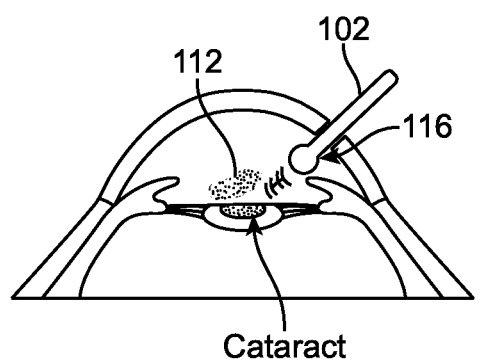
Figure 7C:
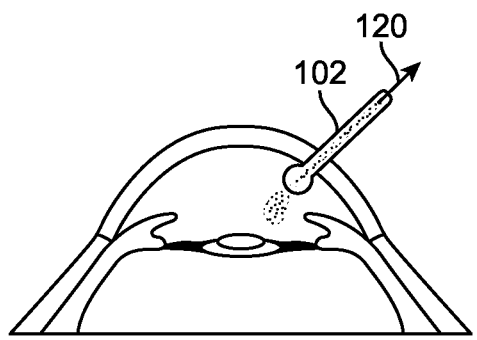

In FIG. 7A, a portion of an eye is shown in cross-section, including a cornea, lens and cataract, with an incision formed in the cornea. The water jet 102 (as described above or some alternative embodiment) may be inserted through the incision, as shown in FIG. 7B. Once the cataract is fully broken up or emulsified, as shown in FIG. 7C, the pieces of cataract may be aspirated. Alternatively, a separate aspiration device may be used. Once the cataract is removed, an intraocular lens (IOL) implant may be implanted, typically through the same incision.

Figure 7D:
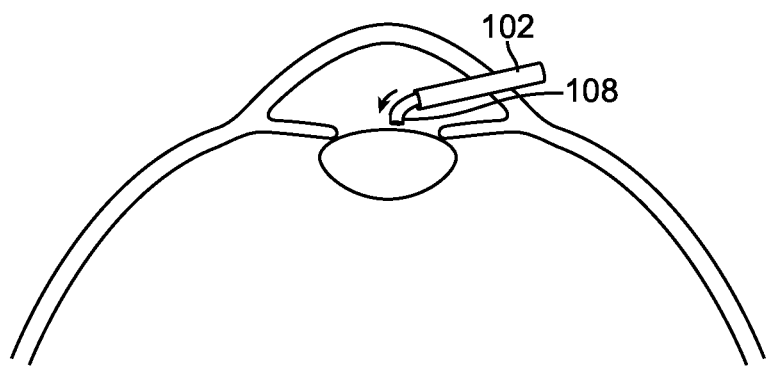
Figure 7F:
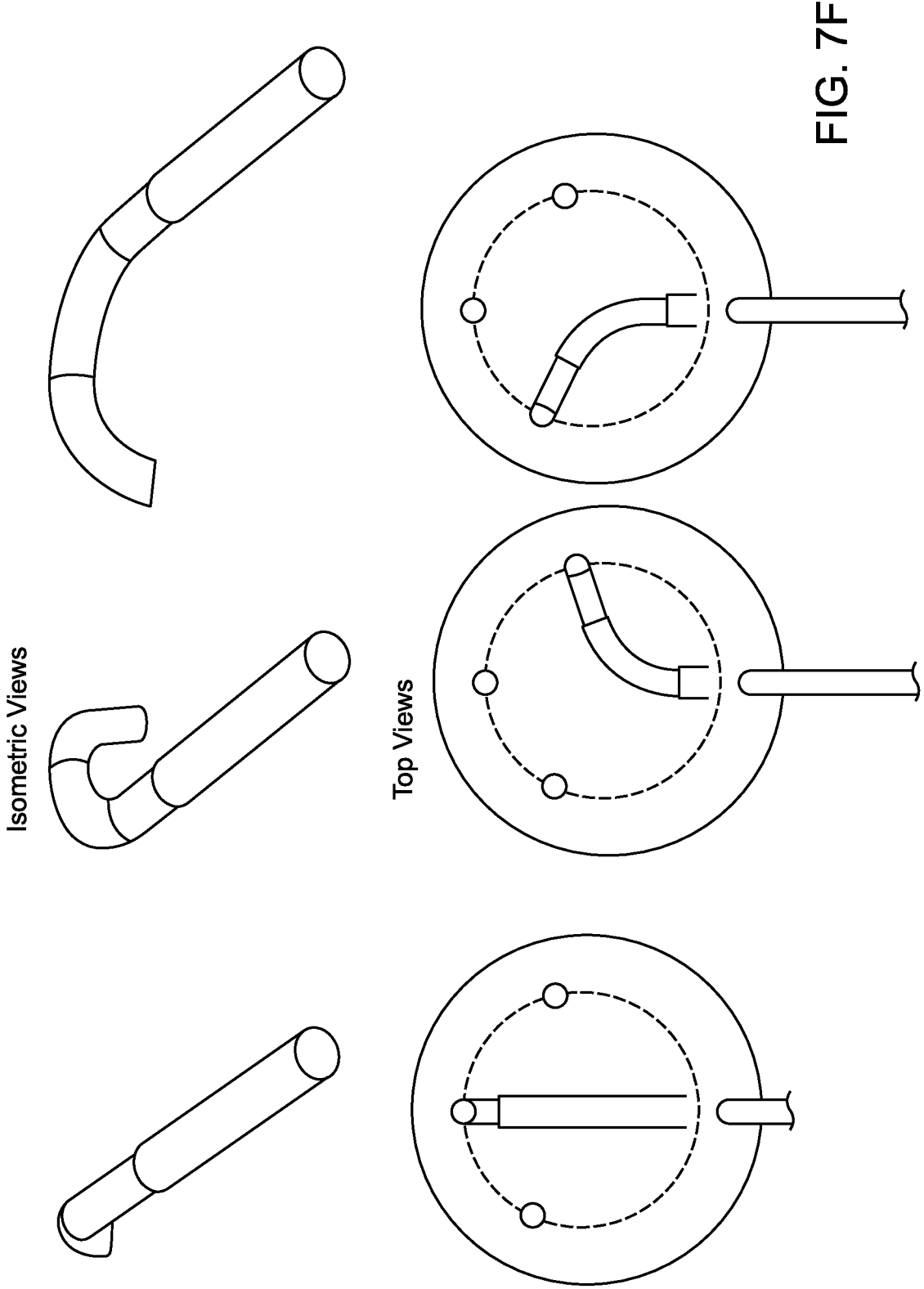
Figure 7G:
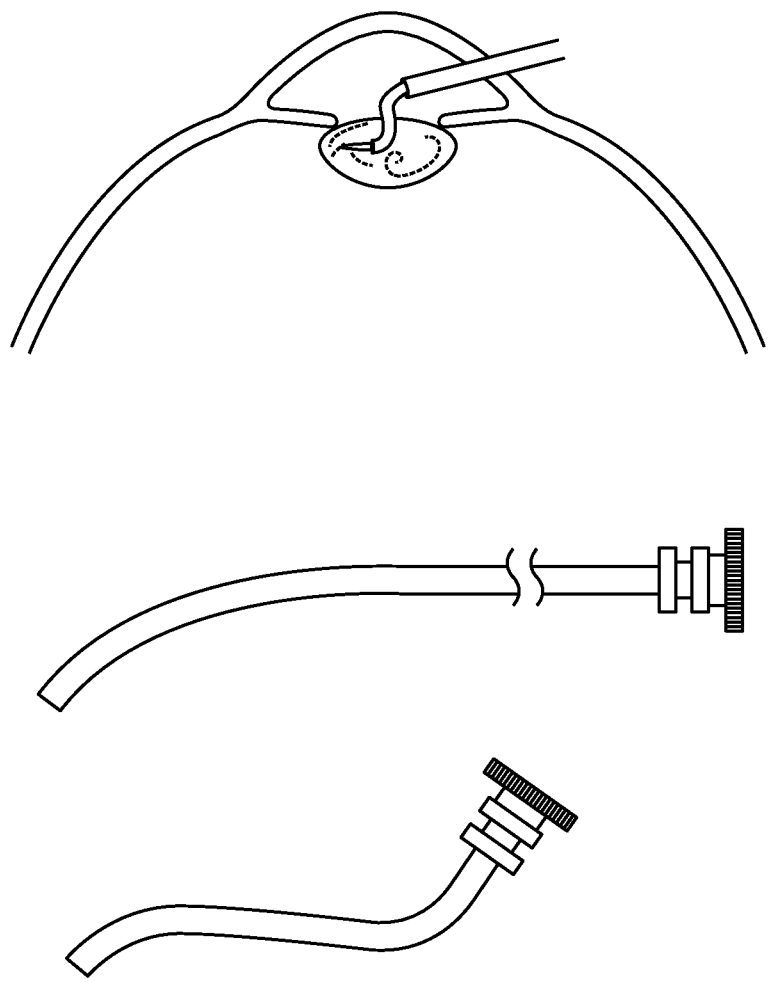

Different instrument configurations for the water jet are depicted in FIG. 7D (bent tube 108 with a nozzle 106), FIG. 7E depicts a pattern of cuts for a circle configuration, as required for a capsulotomy, with a yaw rotation movement of the water jet. The depiction of a circle is for illustrative purposes only, one schooled in the art will realize that other shapes or patterns can be generated manually or under robotic control as required by the surgical procedure. FIG. 7F depicts an isometric view and a top view of a plurality of shaped tubes, axially translatable to vary articulation angle, and configured to reduce proximal motion of the instrument, while enabling complex distal tip motion. FIG. 7G depicts multiple potentially retractable tip configurations for the water jet apparatus.

In alternative embodiments, any other suitable type of articulation mechanism may be used to articulate the water jet apparatus. Examples include, but are not limited to, concentric shaped tubes, flexures, pivot joints, cam mechanisms, pull wire enabled bending, slotted tubes and the like.

Figure 8:
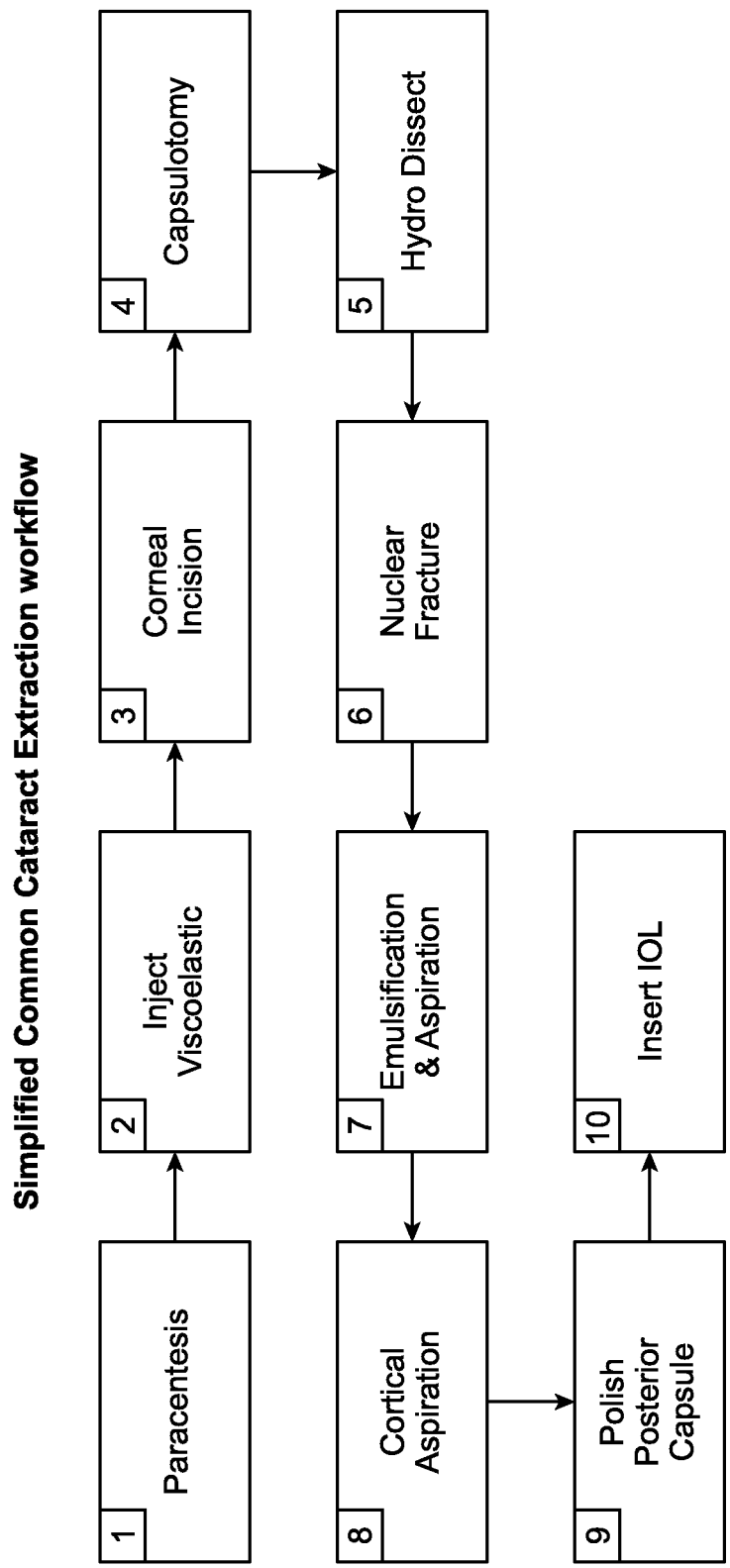
FIG. 8 is a common modern cataract extraction workflow.
Figure 9:
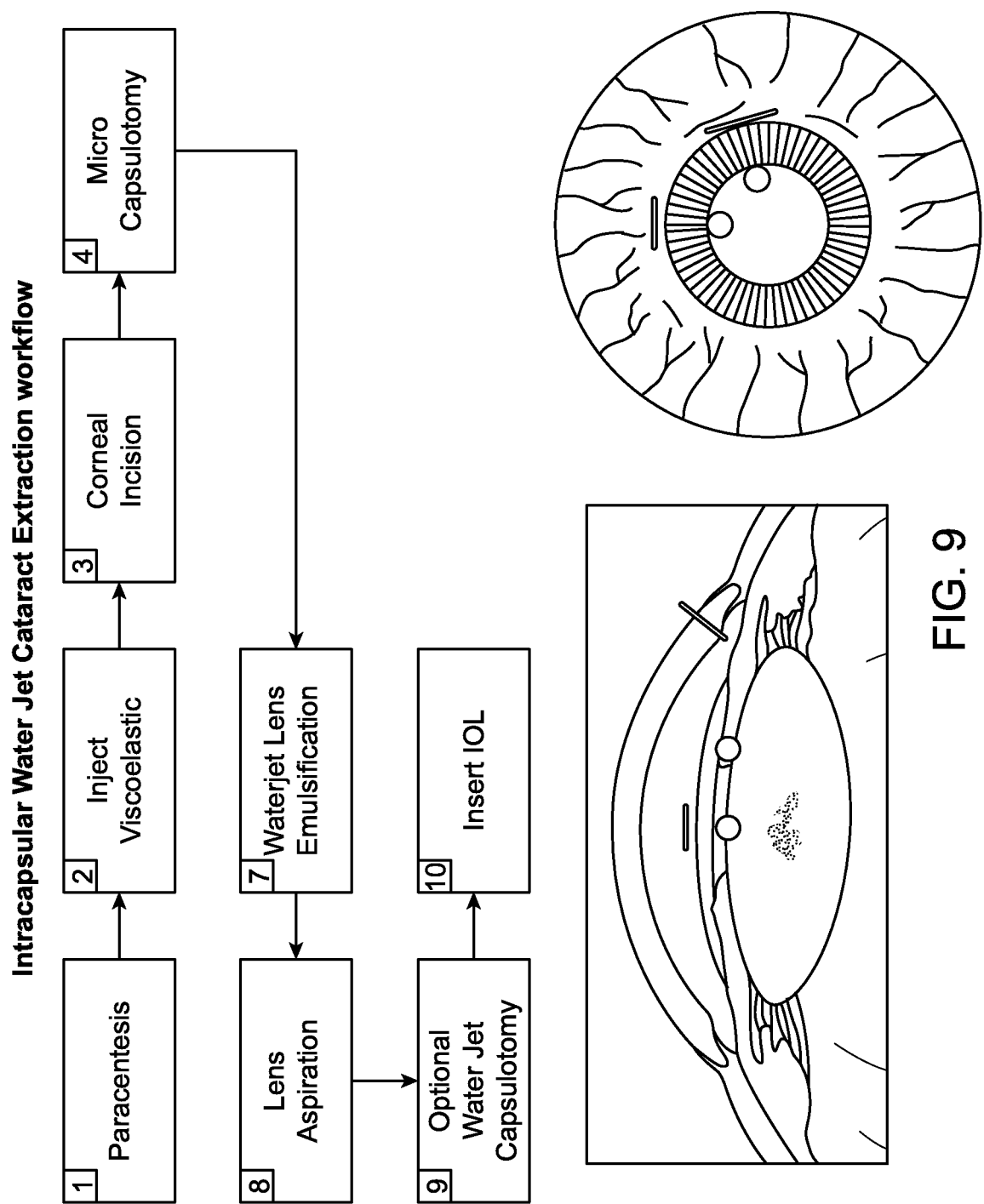
FIGS. 9-11 depict a method for a workflow based at least in part on utilizing the previous examples of a water jet apparatus or water jet system in manual or robotic system control, according to one embodiment of the present invention.
Figure 10:
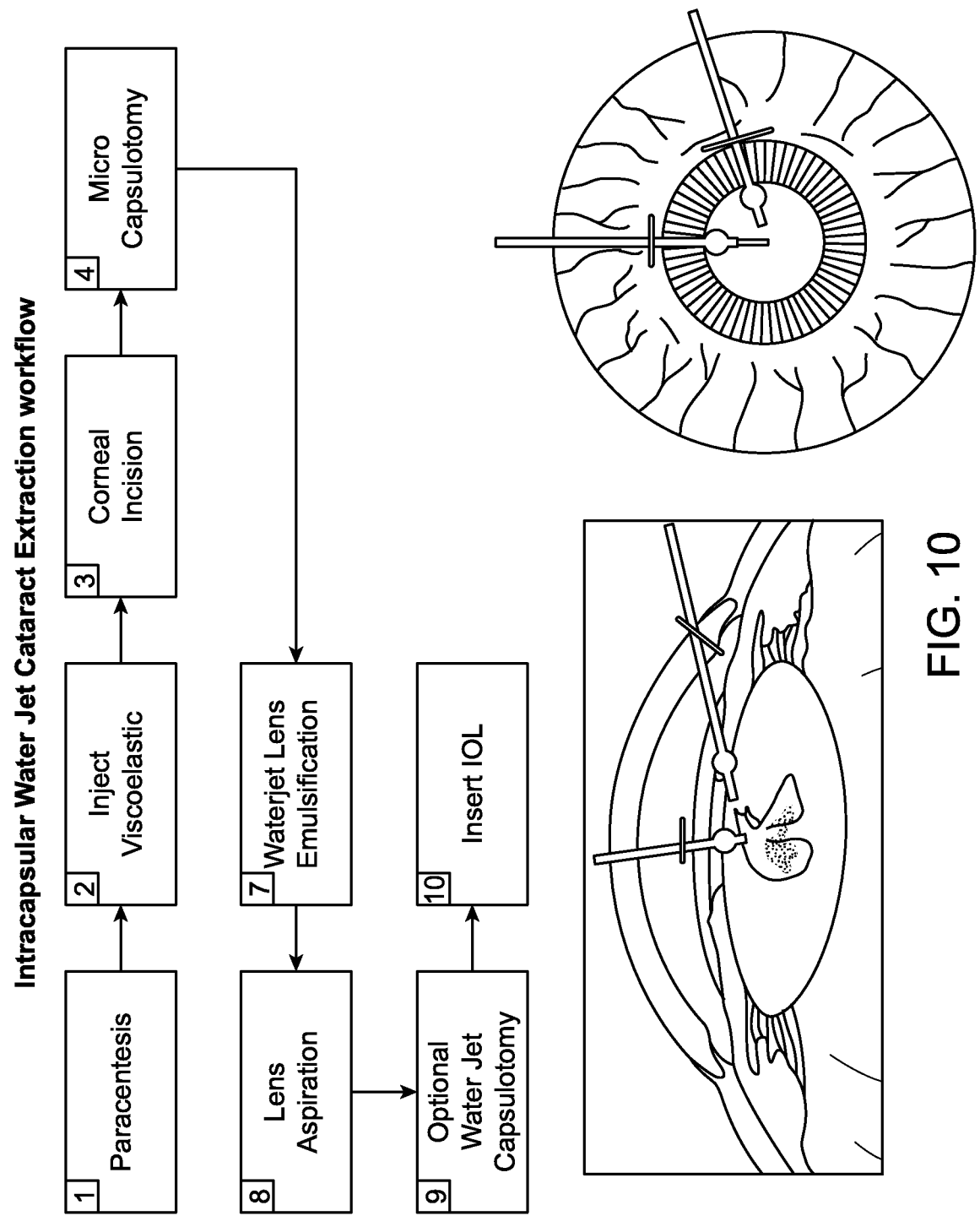
Figure 11:
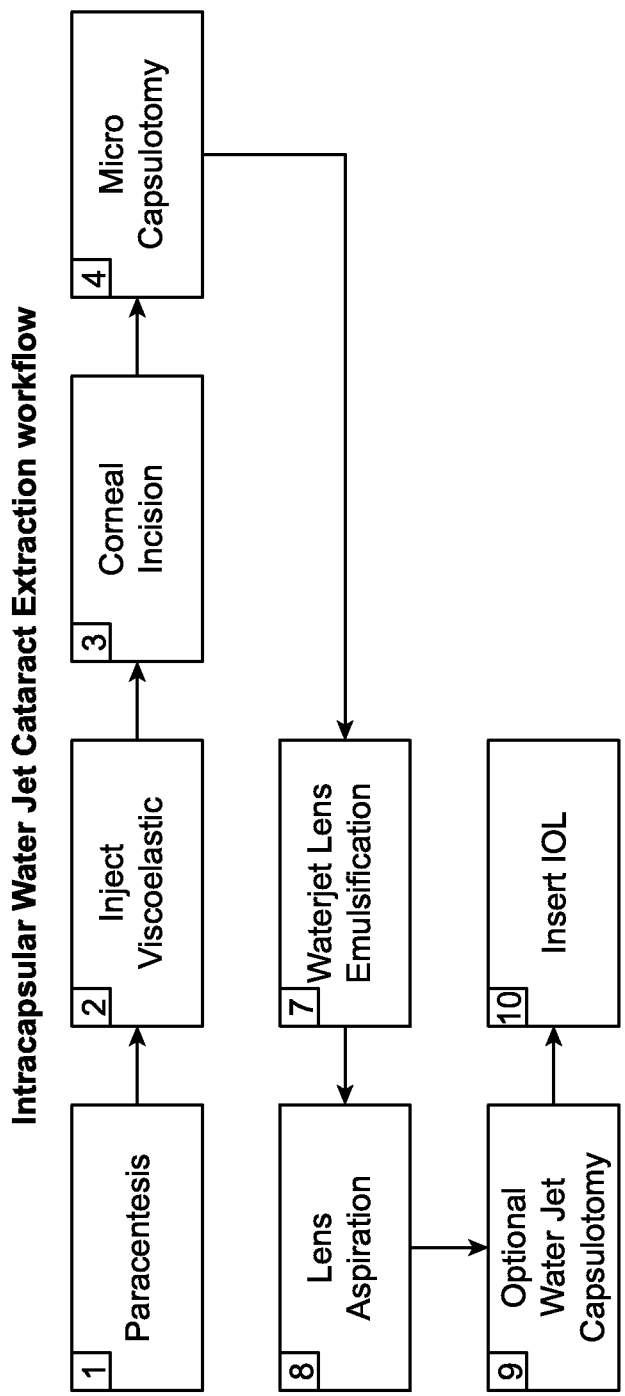

FIGS. 9-11 depict a method for a workflow based at least in part on utilizing the previous examples of a water jet apparatus or water jet system in manual or robotic system control, according to one embodiment of the present invention. The figures include descriptive text to facilitate understanding of the different workflow as compared to FIG. 8.

Elements or components shown with any embodiment herein are exemplary for the specific embodiment and may be used on or in combination with other embodiments disclosed herein. While the invention is susceptible to various modifications and alternative forms, specific examples thereof have been shown in the drawings and are herein described in detail. The invention is not limited, however, to the particular forms or methods disclosed, but to the contrary, covers all modifications, equivalents and alternatives thereof.

What is claimed is:

1. A medical method comprising:
   providing a water jet system, wherein the water jet system comprises a water jet fluid flush tube and an aspiration tube, wherein the water jet fluid flush tube and the aspiration tube are adjacently disposed relative to one another;

endoscopically inserting the water jet system into a patient;

utilizing an ultrasound system to provide an image of the water jet system relative to the patient, the ultrasound system being separate from the water jet system;

applying fluid from the water jet flush tube to create a cutting jet area to break apart tissue;

robotically controlling at least one of a shape and a pattern of cuts by the water jet fluid flush tube to break apart the tissue;

controlling, via a feedback loop, a flow rate of the fluid from the water jet flush tube to treat a target tissue to be broken apart and spare injury to surrounding tissue;

and using the aspiration tube to remove the broken apart tissue via aspiration;

wherein the cutting jet area is controlled based at least in part on a flow rate meter.

2. The medical method of claim 1, wherein during aspiration, a distal tip of the aspiration tube is adjacently disposed relative to a distal tip of the water jet fluid tube.

3. The medical method of claim 1, further comprising attaching the water jet system to an arm.

4. The medical method of claim 3, wherein the arm is a robotic arm, and wherein the robotic arm is coupled to the water jet system via an instrument driver.

5. The medical method of claim 1, wherein the flow rate meter utilizes the feedback loop to control a pump, wherein the feedback loop is controlled by a central processing unit.

6. The medical method of claim 1, wherein the fluid comprises a saline solution.

7. The medical method of claim 1, wherein the water jet system comprises a central processing unit for controlling the aspiration tube.

8. The medical method of claim 1, further comprising moderating a flow of the fluid from the water jet flush tube based on a measured aspiration flow from the aspiration tube.

9. The medical method of claim 8, wherein moderating the flow is based on a throttle valve or pump control.

10. A medical method comprising:

providing a water jet system, wherein the water jet system comprises a water jet fluid flush tube and an aspiration tube, wherein the water jet fluid flush tube and the aspiration tube are adjacently disposed relative to one another;

endoscopically inserting the water jet system into a patient;

utilizing ultrasound to provide an image of the water jet system relative to the patient;

applying fluid from the water jet flush tube to create a cutting jet area to break apart tissue;

robotically controlling at least one of a shape and a pattern of cuts by the water jet fluid flush tube to break apart the tissue;

controlling, via a feedback loop, a flow rate of the fluid from the water jet flush tube to treat a target tissue to be broken apart and spare injury to surrounding tissue; and using the adjacently disposed aspiration tube to remove the broken apart tissue via aspiration;

wherein the cutting jet area is controlled at least in part on a flow rate meter.

11. The medical method of claim 10, further comprising attaching the water jet system to a robotic arm.

12. The medical method of claim 11, wherein the robotic arm is coupled to the water jet system via an instrument driver.

13. The medical method of claim 10, wherein the flow rate meter utilizes the feedback loop to a pump, wherein the feedback loop is controlled by a central processing unit.

14. The medical method of claim 10, further comprising moderating the flow rate of the fluid from the water jet flush tube based on a measured aspiration flow from the aspiration tube, wherein moderating the flow rate is based on a throttle valve or pump control.

\* \* \* \* \*